(12) United States Patent
Phadke et al.

(10) Patent No.: US 7,718,671 B2
(45) Date of Patent: May 18, 2010

(54) SUBSTITUTED ARYLTHIOUREA DERIVATIVES USEFUL AS INHIBITORS OF VIRAL REPLICATION

(75) Inventors: Avinash Phadke, Branford, CT (US); Jesse Quinn, Windsor, CT (US); Junko Ohkanda, Gakuennishi (JP); Andrew Thurkauf, Ridgefield, CT (US); Yiping Shen, Branford, CT (US); Cuixian Liu, Branford, CT (US); Dawei Chen, Middletown, CT (US); Shouming Li, Cheshire, CT (US); Xiangzhu Wang, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 1536 days.

(21) Appl. No.: 10/887,227

(22) Filed: Jul. 8, 2004

(65) Prior Publication Data
US 2005/0032849 A1 Feb. 10, 2005

Related U.S. Application Data

(60) Provisional application No. 60/509,995, filed on Oct. 8, 2003, provisional application No. 60/506,699, filed on Sep. 26, 2003, provisional application No. 60/496,146, filed on Aug. 18, 2003, provisional application No. 60/486,697, filed on Jul. 10, 2003.

(51) Int. Cl.
*A61K 31/47* (2006.01)
*C07D 217/02* (2006.01)
*A61K 31/445* (2006.01)
*C07D 211/32* (2006.01)
*C07C 335/00* (2006.01)

(52) U.S. Cl. .................. 514/307; 546/144; 546/233; 514/331; 564/27

(58) Field of Classification Search .............. 560/19; 514/506, 317, 467, 307, 331; 549/452; 546/144, 546/233; 564/27
See application file for complete search history.

(56) References Cited

U.S. PATENT DOCUMENTS

| 4,194,008 A | 3/1980 | Enders et al. |
| 4,307,106 A | 12/1981 | Lombardino |
| 6,492,403 B1 | 12/2002 | Illig et al. |
| 6,521,754 B2 | 2/2003 | Alanine et al. |
| 6,534,546 B1 | 3/2003 | Honda et al. |
| 6,677,360 B2 | 1/2004 | Albers et al. |
| 6,696,487 B2 | 2/2004 | Gerusz et al. |

FOREIGN PATENT DOCUMENTS

| DE | 26 39 738 A1 | 3/1978 |
| EP | 0 806 205 A2 | 11/1997 |
| GB | 1 408 198 | 10/1975 |
| GB | 1 571 970 | 7/1980 |

| WO | WO 98/42667 | 10/1998 |
| WO | WO 01/83429 A1 | 11/2001 |
| WO | WO 02/090336 A1 | 11/2002 |

OTHER PUBLICATIONS

Goodyer et. al., "Synthesis of N-Benzyl-and N-Phenyl-2-amino-4,5-dihydrothiazoles and Thioureas and Evaluation as Modulators of the Isoforms of Nitric Oxide Synthase", Bioorganic & Medicinal Chemistry 11 (2003), 4189-4206.*
Walker et. al., "Promising candidates for the treatment of chronic hepatitis C", Expert Opinion and Investigational Drugs (2003) 12(8):1269-1280.*
HCV RNA-depednent RNA polymerase as a target for antiviral development, Current Opinion in Pharmacology. 2002, 2 (5), 534-540.*
Leveque et. al., "RNA-dependent RNA polymerase encoded by hepatitis C virus: biomedical applications", Cell. Mol. Life S ci. 59, 2002, 909-919.*
Hcaplus 88:36734, "Mass spectra of ortho substituted 1-phenyl-2-thioureas", Grehn, Leif, 1977.*
International Search Report; International Appln No. PCT/US2004/022599; Date of mailing: Dec. 28, 2004 (7 pgs).
Written Opinion for International Appln No. PCT/US2004/022599; Date of mailing: Dec. 28, 2004 (7 pgs).
Ludovici, Donald W., et al Evolution of Anti-HIV Drug Candidates. Part I: From Alpha-Anilinophenylacetamide (Alpha-APA) to Imidoyl Thiourea (ITU) Bioorganic & Medicinal Chemistry Letters 11 (2001) pp. 2225-2228.

(Continued)

*Primary Examiner*—Janet L Andres
*Assistant Examiner*—Binta M Robinson
(74) *Attorney, Agent, or Firm*—Cantor Colburn LLP

(57) ABSTRACT

Substituted arylthiourea compounds of Formula I,

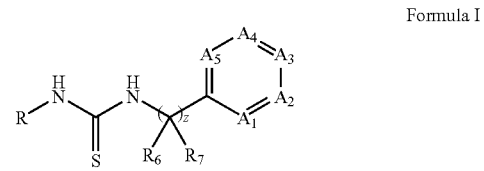

Formula I and the pharmaceutically acceptable salts of such compounds, useful as antiviral agents, are provided herein. Certain substituted arylthioureas disclosed herein are potent and/or selective inhibitors of viral replication, particularly Hepatitis C virus replication. Pharmaceutical compositions containing one or more substituted arylthiourea compounds and one or more pharmaceutically acceptable carriers, excipients, or diluents are provided herein. Such pharmaceutical compositions may contain a substituted arylthiourea as the only active agent or may contain a combination of a substituted arylthiourea derivative and one or more other pharmaceutically active agents. Methods of treating Hepatitis C viral infections in mammals are also provided herein.

22 Claims, No Drawings

OTHER PUBLICATIONS

Hungarian Patent No. HU 155444; Dec. 23, 1968 (translation of abstract only).

Kaldrikyan, M.A., et al. "Pyrimidine derivatives. XIX. N-Substituted thiobarbituric and barbituric acids", Armyanski Khimicheskii Zhurnal (1971), 24(10), 913-17. Journal written in Russian (translation of abstract only).

Koch, Klaus R., et al. "Determination of the nucleophilic reactivity constants for a series of N-(n-propyl)-$N^1$-(para-R-benzoyl)thioureas towards trans-[Pt(pyridine)2C12]" Inorganica Chimica Acta 331 (2002) 136-142.

Rasmussen, C.R., et al. "Improved Procedures for the Preparation of Cycloalkyl-, Arylalkyl-, and Arylthioureas1" Synthesis 1988, (6) 456-9.

Szilagyi, G., et al "Substituted benzyl- and benzoylurea derivatives of anticonvulsant activity" Acta Pharmaceutica Hungarica (1975), 45(4), 145-54. Journal written in Hungarian (translation of abstract only).

Urbahns, Klaus, et al. "Biphenyls as Potent Vitronectin Receptor Antagonists" Bioorganic & Medicinal Chemistry Letters 12 (2002) 205-208.

SciFinder search provided by inventor, Jul. 1, 2004 (5 pgs).
SciFinder search provided by inventor, Jul. 1, 2004 (8 pgs).
SciFinder search provided by inventor, Jul. 1, 2004 (32 pgs).
SciFinder search provided by inventor, Jul. 1, 2004 (25 pgs).
SciFinder search provided by inventor, Jul. 1, 2004 (18 pgs).
SciFinder search provided by inventor, Jul. 1, 2004 (27 pgs).
SciFinder search provided by inventor, Jul. 1, 2004 (94 pgs).

* cited by examiner

SUBSTITUTED ARYLTHIOUREA DERIVATIVES USEFUL AS INHIBITORS OF VIRAL REPLICATION

CROSS-REFERENCE TO RELATED APPLICATIONS

This application claims priority to U.S. provisional applications 60/486,697 filed Jul. 10, 2003, 60/496,146 filed Aug. 18, 2003, 60/506,699 filed Sep. 26, 2003, and 60/509,995 filed Oct. 8, 2003 which are hereby incorporated by reference in their entirety.

FIELD OF THE INVENTION

Substituted arylthiourea compounds, possessing antiviral activity are disclosed herein. Certain substituted arylthioureas disclosed herein are potent and/or selective inhibitors of viral replication, particularly Hepatitis C virus replication. Pharmaceutical compositions containing one or more substituted arylthiourea compounds and one or more pharmaceutically acceptable carriers, excipients, or diluents are also provided herein. Such pharmaceutical compositions may contain a substituted arylthiourea as the only active agent or may contain a combination of a substituted arylthiourea derivative and one or more other pharmaceutically active agents. Methods for treating Hepatitis C viral infections in mammals are further provided herein.

BACKGROUND

In the 1940's the disease originally referred to as viral hepatitis was differentiated into two separate disorders termed infectious hepatitis (hepatitis A, HAV) and homologous serum hepatitis (hepatitis B, HBV). Transfusion of blood products had been demonstrated to be a common route of transmission of viral hepatitis. HBV was originally assumed to be the causative agent of post-transfusion hepatitis as the epidemiological and clinical features of the disorder did not fit those of HAV.

Soon after a radioimmunoassay for hepatitis B surface antigen (HBsAg) became available as a tool for identifying patients infected with HBV, it became apparent that most patients having post-transfusion hepatitis were negative for HBsAg. Thus, hepatitis following blood transfusion that was not caused by hepatitis A or hepatitis B and was subsequently referred to as non-A, non-B hepatitis.

The causative agent of non-A, non-B hepatitis (hepatitis C virus, HCV) was discovered in 1989 via screening of cDNA expression libraries made from RNA and DNA from chimpanzees infected with serum from a patient with post-transfusion non-A, non-B hepatitis. To identify portions of the genome that encoded viral proteins, the libraries were screened with antibodies from patients who had non-A, non-B hepatitis. These investigators went on to show that the virus they identified was responsible for the vast majority of cases of non-A, non-B hepatitis.

The hepatitis C virus is one of the most prevalent causes of chronic liver disease in the United States. It accounts for about 15 percent of acute viral hepatitis, 60 to 70 percent of chronic hepatitis, and up to 50 percent of cirrhosis, end-stage liver disease, and liver cancer. Almost 4 million Americans, or 1.8 percent of the U.S. population, have antibodies to HCV (anti-HCV), indicating ongoing or previous infection with the virus. Hepatitis C causes an estimated 8,000 to 10,000 deaths annually in the United States. Hepatitis C virus (HCV) infection occurs throughout the world, and, prior to its identification, represented the major cause of transfusion-associated hepatitis. The seroprevalence of anti-HCV in blood donors from around the world has been shown to vary between 0.02% and 1.23%. HCV is also a common cause of hepatitis in individuals exposed to blood products. There have been an estimated 150,000 new cases of HCV infection each year in the United States alone during the past decade. The acute phase of HCV infection is usually associated with mild symptoms. However, evidence suggests that only 15%-20% of the infected people will clear HCV. Among the group of chronically infected people, 10-20% will progress to life-threatening conditions known as cirrhosis and another 1-5% will develop a liver cancer called hepatocellular carcinoma. Unfortunately, the entire infected population is at risk for these life-threatening conditions because no one can predict which individual will eventually progress to any of them.

HCV is a small, enveloped, single-stranded positive RNA virus in the Flaviviridae family. The genome is approximately 10,000 nucleotides and encodes a single polyprotein of about 3,000 amino acids. The polyprotein is processed by host cell and viral proteases into three major structural proteins and several non-structural proteins necessary for viral replication. Several different genotypes of HCV with slightly different genomic sequences that correlate with differences in response to treatment with interferon alpha have since been identified.

HCV replicates in infected cells in the cytoplasm, in close association with the endoplasmic reticulum. Incoming positive sense RNA is released and translation is initiated via an internal initiation mechanism. Internal initiation is directed by a cis-acting RNA element at the 5' end of the genome; some reports have suggested that full activity of this internal ribosome entry site, or IRES, is seen with the first 700 nucleotides, which spans the 5' untranslated region (UTR) and the first 123 amino acids of the open reading frame (ORF). All the protein products of HCV are produced by proteolytic cleavage of a large (approximately 3000 amino acid) polyprotein, carried out by one of three proteases: the host signal peptidase, the viral self-cleaving metalloproteinase, NS2, or the viral serine protease NS3/4A. The combined action of these enzymes produces the structural proteins (C, E1 and E2) and non-structural (NS2, NS3, NS4A, NS4B, NS5A, and NS5B) proteins that are required for replication and packaging of viral genomic RNA. NS5B is the viral RNA-dependent RNA polymerase (RDRP) that is responsible for the conversion of the input genomic RNA into a negative stranded copy (complimentary RNA, or cRNA; the cRNA then serves as a template for transcription by NS5B of more positive sense genomic/messenger RNA.

An effective vaccine is greatly needed, yet development is unlikely in the near future because: i) lack of an efficient cell culture system and small animal models; ii) a weak neutralizing humoral and protective cellular immune response; iii) marked genetic variability of the virus, and iv) the lack of a viral proofreading mechanism.

Several institutions and laboratories are attempting to identify and develop anti-HCV drugs. Currently the only effective therapy against HCV is alpha-interferon, which reduces the amount of virus in the liver and blood (viral load) in only a small proportion of infected patients. Alpha interferon was first approved for use in HCV treatment more than ten years ago. Alpha interferon is a host protein that is made in response to viral infections and has natural antiviral activity. These standard forms of interferon, however, are now being replaced by pegylated interferons (peginterferons). Peginterferon is alpha interferon that has been modified chemically by the addition of a large inert molecule of polyethylene glycol.

At the present time, the optimal regimen appears to be a 24- or 48-week course of the combination of pegylated alpha interferon and the nucleoside Ribavarin, an oral antiviral agent that has activity against a broad range of viruses. By itself, Ribavarin has little effect on HCV, but adding it to interferon increases the sustained response rate by two- to three-fold. Nonetheless, response rates to the combination interferon/Ribavarin therapy are moderate, in the range 50-60%, although response rates for selected genotypes of HCV (notably genotypes 2 and 3) are typically higher. Among patients who become HCV RNA negative during treatment, a significant proportion relapse when therapy is stopped.

In addition, there are often significant adverse side effects associated with each of these agents. Patients receiving interferon often present with flu-like symptoms. Pegylated interferon has been associated with bone marrow suppressive effects. Importantly, alpha interferon has multiple neuropsychiatric effects. Prolonged therapy can cause marked irritability, anxiety, personality changes, depression, and even suicide or acute psychosis. Interferon therapy has also been associated with relapse in people with a previous history of drug or alcohol abuse.

Side effects of Ribavarin treatment include histamine-like side effects (itching and nasal stuffiness) and anemia due to dose related hemolysis of red cells and histamine like side effects.

Taken together, the proceeding facts indicate a significant need for effective small molecule inhibitors of hepatitis C virus replication that do not suffer from the above-mentioned drawbacks. Certain compounds provided herein meet these requirements and possess additional advantages.

SUMMARY OF THE INVENTION

Compounds of Formula I (shown below) are provided herein. Formula I includes substituted arylthiourea derivatives and related compounds, certain of which possess antiviral activity. Other embodiments provide compounds of Formula I that are potent and/or selective inhibitors of Hepatitis C virus replication. Additionally pharmaceutical compositions containing one or more compound of Formula I, or a salt, solvate, or acylated prodrug of such compounds, and one or more pharmaceutically acceptable carriers, excipients, or diluents are provided herein.

Methods of treating patients suffering from certain infectious diseases comprising administering to such patients an amount of a compound of Formula I effective to reduce signs or symptoms of the disease or disorder are also provided herein. These infectious diseases include viral infections, particularly HCV infections. The invention includes methods of treating human patients suffering from an infectious disease, but also encompasses methods of treating other animals, including livestock and domesticated companion animals, suffering from an infectious disease.

A method of inhibiting HCV replication in vivo comprising administering to a patient infected with HCV a concentration of a compound or salt of Formula I sufficient to inhibit HCV replicon replication in vitro is also provided herein.

Methods of treatment include administering a compound of Formula I as a single active agent or administering a compound of Formula I in combination with one or more other therapeutic agents.

Thus in a first aspect the invention includes compounds and pharmaceutically acceptable

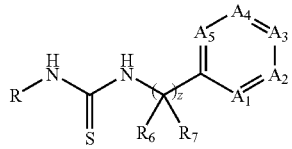

Formula I

Within Formula I $z$ is 0, 1, or 2.

R is hydrogen, methyl, or ethyl.

$A_1$ is nitrogen or $CR_1$; $A_2$ is nitrogen or $CR_2$; $A_3$ is nitrogen or $CR_3$; $A_4$ is nitrogen or $CR_4$; and $A_5$ is nitrogen or $CR_5$; where zero or one of $A_1$, $A_2$, $A_3$, $A_4$, or $A_5$ is nitrogen.

$R_1$, $R_4$, and $R_5$ are each independently hydrogen, hydroxy, amino, halogen, cyano, $C_1$-$C_4$alkyl, $C_1$-$C_4$alkoxy, $C_1$-$C_2$haloalkyl, or $C_1$-$C_2$haloalkoxy.

One of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is (i) $C_3$-$C_6$alkyl or $C_3$-$C_6$alkoxy, substituted with at least one $C_1$-$C_4$alkoxy or mono- or di-$C_1$-$C_4$alkylamino;

(ii) $C_4$-$C_8$alkoxycarbonyl, $C_5$-$C_8$alkyl, $C_5$-$C_8$alkenyl, $C_5$-$C_8$alkynyl; or $C_4$-$C_8$alkoxy;

(iii) (phenyl)L- or (pyridyl)L-, each of which is optionally fused to a 6-membered carbocyclic ring or a 5- or 6-membered heterocyclic ring containing 1 or 2 heteroatoms independently chosen from N, O, and S, where L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl-; or (iv) ($C_5$-$C_7$cycloalkyl)L- or (heterocycloalkyl)L-, each of which is optionally bridged and each of which is optionally fused to a 6-membered carbocyclic ring or 6-membered heterocyclic ring containing 1 or 2 heteroatoms independently chosen from N, O, and S; wherein each of (i), (ii), (iii), and (iv), is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, phenyl, and pyridyl.

$R_6$ and $R_7$, when present, are independently chosen from hydrogen, halogen, $C_1$-$C_4$alkyl, $C_1$-$C_4$alkoxy, and phenyl; or $R_6$ and $R_7$ may be joined to form a 3- to 7-membered cycloalkyl ring.

An alternate embodiment provides compounds and pharmaceutically acceptable salts of Formula I in which R is hydrogen, methyl, or ethyl.

$z$ is 2.

$A_1$ is nitrogen or $CR_1$; $A_2$ is nitrogen or $CR_2$; $A_3$ is nitrogen or $CR_3$; $A_4$ is nitrogen or $CR_4$; and $A_5$ $CR_5$; where zero or one of $A_1$, $A_2$, $A_3$, or $A_4$ is nitrogen.

$R_1$ and $R_4$ are each independently hydrogen, hydroxy, amino, halogen, cyano, $C_1$-$C_4$alkyl, $C_1$-$C_4$alkoxy, $C_1$-$C_2$haloalkyl, or $C_1$-$C_2$haloalkoxy.

One of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is (i) hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy (ii) $C_3$-$C_6$alkyl or $C_3$-$C_6$alkoxy, substituted with at least one $C_1$-$C_4$alkoxy or mono- or di-$C_1$-$C_4$alkylamino;

(iii) $C_4$-$C_8$alkoxycarbonyl, $C_5$-$C_8$alkyl, $C_5$-$C_8$alkenyl, $C_5$-$C_8$alkynyl; or $C_4$-$C_8$alkoxy;

(iv) (phenyl)L- or (pyridyl)L-, each of which is optionally fused to a 6-membered carbocyclic ring or a 5- or 6-membered heterocyclic ring containing 1 or 2 heteroatoms independently chosen from N, O, and S, where L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl-; or (v) ($C_5$-$C_7$cycloalkyl)L- or (heterocycloalkyl)L-, each of which is optionally bridged and each of which is optionally fused to a 6-membered carbocyclic ring or 6-membered heterocyclic ring containing 1 or 2 heteroatoms independently chosen from N, O, and S; wherein each of (ii), (iii), (iv), and (v), is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl) amino, $C_2$-$C_6$alkoxycarbonyl, $C_1$-$C_2$haloalkyl, $C_1$-$C_2$haloalkoxy, phenyl, and pyridyl.

$R_5$ is joined with one of $R_6$ to form a fused 5- to 7-membered cycloalkyl ring; and the other of $R_6$ and both $R_7$ are independently chosen from hydrogen, halogen, $C_1$-$C_4$alkyl, $C_1$-$C_4$alkoxy, and phenyl.

Certain substituted aryl thioureas disclosed herein exhibit good activity in an HCV replication assay, such as the HCV replicon assay set forth in Example 9, which follows. Preferred substituted aryl thioureas exhibit an $EC_{50}$ of about 10 micromolar or less, or more preferably an $EC_{50}$ of about 1 micromolar or less; or an $EC_{50}$ of about 500 nanomolar or less in an HCV replicon assay.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature.

Formula I includes all subformulae described herein. For example Formula I includes compounds and pharmaceutically acceptable salts of Formulas IA-IC and Formulas 2-19, In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. R, $A_1$-$A_5$, $R_1$-$R_7$. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —COOH is attached through the carbon atom.

As used herein, "alkyl" is intended to include both branched and straight-chain saturated aliphatic hydrocarbon groups, having the specified number of carbon atoms. Thus, the term $C_1$-$C_6$alkyl as used herein includes alkyl groups having from 1 to about 6 carbon atoms. When $C_0$-$C_n$ alkyl is used herein in conjunction with another group, for example, phenyl$C_0$-$C_4$alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates hydrocarbon chains of either a straight or branched configuration comprising one or more unsaturated carbon-carbon bonds, which may occur in any stable point along the chain, such as ethenyl and propenyl.

"Alkynyl" as used herein, indicates hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

The term "alkoxycarbonyl" indicates an alkoxy group, as defined above, having the indicated number of carbon atoms, attached through a keto linkage. The carbon of the keto linker is not included in the numbering, thus a $C_2$alkoxycarbonyl has the formula $CH_3CH_2O(C=O)$—.

The term "alkylcarboxamide" indicates an alkyl group, as defined above, having the indicated number of carbon atoms, attached through a carboxamide linkage, i.e. a —$CONH_2$ linkage, where one or both of the amino hydrogen is replace by an alkyl group. Alkylcarboxamide groups may be mono- or di-alkylcarboxamide groups, such an ethylcarboxamide or dimethylcarboxamide.

As used herein, the term "mono- or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term (aryl)carbhydryl, aryl and carbhydryl are as defined above and the point of attachment is on the carbhydryl group, for example a phenylpropen-1-yl group.

"Carbhydryl" as used herein, includes both branched and straight-chain hydrocarbon groups, which are saturated or unsaturated, having the specified number of carbon atoms.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norbornane or adamantane.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. In the term "heteroarylalkyl," heteroaryl and alkyl are as defined above, and the point of attachment is on the alkyl group. This term encompasses, but is not limited to, pyridylmethyl, thiophenylmethyl, and pyrrolyl(1-ethyl).

The term "heterocycloalkyl" is used to indicate saturated cyclic groups containing from 1 to about 3 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$heterocycloalkyl group contains from 2 to about 7 carbon ring atoms and at least one ring atom chosen from N, O, and S. Examples of heterocycloalkyl groups include morpholinyl, piperazinyl, piperidinyl, and pyrrolidinyl groups.

A fused "6-membered carbocyclic or 5- or 6-membered heterocyclic ring" is a saturated, partially unsaturated or aromatic ring having the indicated number of ring atoms which forms a bicyclic ring system with the group to which it is fused. 6-membered carbocyclic rings include phenyl, cyclohexyl, and cycloalkenyl. 5- and 6-membered heterocyclic rings contain 1, 2, or 3 heteroatoms independently chosen from N, S, and O, for example pyridyl, piperidinyl, pyrrolidinyl, and morpholinyl groups.

"(Phenoxy)alkyl" is a phenoxy group attached through an alkyl linker having the indicated number of carbon atoms. When the alkyl linker is a $C_0$ alkyl the phenoxy group is bound to the group it substitutes through it oxygen atom, e.g. phenyl-O—. Similarly "(phenyl)alkoxy" is a phenyl group attached through an alkoxy linker having the indicated number of carbon atoms, for example a phenylmethoxy substituent, phenyl-$CH_2$—O— and "(phenyl)alkylamino is a phenyl group attached through an amino group, usually a secondary amino group, having the indicated number of carbon atoms.

"Pharmaceutically acceptable salts" includes derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

The term "prodrugs" includes any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "therapeutically effective amount" of a compound of this invention means an amount effective, when administered to a human or non-human patient, to provide a therapeutic benefit such as an amelioration of symptoms, e.g., an amount effective to decrease the symptoms of a viral infection, and preferably an amount sufficient to reduce the symptoms of an HCV infection. In certain circumstances a patient suffering from a viral infection may not present symptoms of being infected. Thus a therapeutically effective amount of a compound is also an amount sufficient to prevent a significant increase or significantly reduce the detectable level of virus or viral antibodies in the patient's blood, serum, or tissues. A significant increase or reduction in the detectable level of virus or viral antibodies is any detectable change that is statistically significant in a standard parametric test of statistical significance such as Student's T-test, where $p<0.05$.

A "replicon" as used herein includes any genetic element, for example, a plasmid, cosmid, bacmid, phage or virus, that is capable of replication largely under its own control. A replicon may be either RNA or DNA and may be single or double stranded.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule can be described herein according to the normal convention of providing the sequence in the 5' to 3' direction.

Viral Replication Inhibitors

In addition to compounds of Formula I, described above in the "Summary of Invention" section compounds and pharmaceutically acceptable salts of Formula IA, which have the same chemical formula and compounds of Formula I, but in which the variables, e.g. z, $A_1$-$A_5$, R, and $R_1$-$R_7$ have the values set forth below are also provided herein.

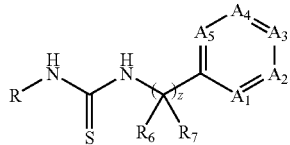

Formula I

Within Formula IA:

z is 0, 1, or 2.

R is hydrogen, methyl, or ethyl.

$A_1$ is nitrogen or $CR_1$; $A_2$ is nitrogen or $CR_2$; $A_3$ is nitrogen or $CR_3$; $A_4$ is nitrogen or $CR_4$; and $A_5$ is nitrogen or $CR_5$; where zero or one of $A_1$, $A_2$, $A_3$, $A_4$, or $A_5$ is nitrogen.

$R_1$, $R_4$, and $R_5$ are each independently hydrogen, hydroxy, amino, halogen, cyano, $C_1$-$C_4$alkyl, $C_1$-$C_4$alkoxy, $C_1$-$C_2$haloalkyl, or $C_1$-$C_2$haloalkoxy;

When z is 0; one of $R_2$ and $R_3$ is hydrogen, hydroxy, amino, cyano, halogen, $C_1$-$C_6$alkyl, $C_1$-$C_0$alkoxy, $C_1$-$C_2$haloalkyl, or $C_1$-$C_2$haloalkoxy; and the other of $R_2$ and $R_3$ is (a) $C_3$-$C_6$alkyl or $C_3$-$C_6$alkoxy, each of which is substituted with at least one $C_1$-$C_4$alkoxy or mono- or di-$C_1$-$C_4$alkylamino;

(b) $C_4$-$C_8$alkoxycarbonyl;

(c) (phenyl)$C_1$-$C_2$alkoxy, (phenyl)$C_1$-$C_2$alkylamino, (phenylamino)$C_1$-$C_2$alkyl, (phenoxy)$C_1$-$C_2$alkyl, and (pyridyl)L-, where L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl-;

(d) (cyclopentyl)L- or (pyrrolidinyl)L-, (e) (cyclohexyl)$C_0$-$C_2$alkyl, (cyclopentyl)$C_0$-$C_2$alkyl, (piperidinyl)$C_0$-$C_2$alkyl or (pyrrolidinyl)$C_0$-$C_2$alkyl, each of which is fused to a 6-membered carbocyclic ring or 6-membered heterocyclic ring containing 1 or 2 heteroatoms independently chosen from N, O, and S; or (f) (phenyl)$C_0$-$C_2$alkyl or (pyridyl)$C_0$-$C_2$alkyl, each of which is fused to a 5- or 6-membered heterocycloalkyl group containing 1 or 2 oxygen atoms.

Wherein each of (a), (b), (c), (d), (e), and (f) is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_4$alkanoyl, $C_1$-$C_6$alkoxycarbonyl, $C_1$-$C_2$haloalkyl, $C_1$-$C_2$haloalkoxy, phenyl, and pyridyl.

Or the other of $R_2$ and $R_3$ may be (g) cyclohexyl, piperidinyl, bridged cyclohexyl, or bridged piperidinyl, each of which is substituted with at least one substituent chosen from $C_2$-$C_6$alkoxycarbonyl, phenyl, pyridyl, $C_4$-$C_8$ alkyl, and $C_4$-$C_8$alkoxy; and further substituted with 0 to 3 substituents independently chosen from, hydroxy, amino, cyano, halogen, $C_1$-$C_6$alkyl, $C_1$-$C_6$alkoxy, $C_1$-$C_2$haloalkyl, and $C_1$-$C_2$haloalkoxy.

Or one of $R_2$ and $R_3$ is halogen, $C_1$-$C_2$alkoxy, $C_1$-$C_2$haloalkyl, or $C_1$-$C_2$haloalkoxy, and the other is cyclohexyl, piperidinyl, $C_5$-$C_8$alkyl, $C_5$-$C_8$alkenyl $C_5$-$C_8$alkynyl, or $C_4$-$C_8$alkoxy.

When z is 1 or 2; provided that $R_2$ is not benzyloxy or cyclopentyloxy when $R_3$ is methoxy; one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is (i) $C_3$-$C_6$alkyl or $C_3$-$C_6$alkoxy, substituted with at least one $C_1$-$C_4$alkoxy or mono- or di-$C_1$-$C_4$alkylamino;

(ii) $C_4$-$C_8$alkoxycarbonyl, $C_5$-$C_8$alkenyl, or $C_5$-$C_8$alkynyl;

(iii) (phenyl)L- or (pyridyl)L-, each of which is optionally fused to a 6-membered carbocyclic ring or a 5- or 6-membered heterocyclic ring containing 1 or 2 heteroatoms independently chosen from N, O, and S;

(iv) ($C_5$-$C_7$cycloalkyl)L- or (heterocycloalkyl)L-, each of which is optionally bridged and each of which is optionally fused to a 6-membered carbocyclic ring or 6-membered heterocyclic ring containing 1 or 2 heteroatoms independently chosen from N, O, and S.

Wherein each of (i), (ii), (iii), and (iv), is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, phenyl, and pyridyl.

Or one of $R_2$ and $R_3$ is halogen, $C_1$-$C_2$alkoxy, $C_1$-$C_2$haloalkyl, or $C_1$-$C_2$haloalkoxy, and the other is $C_5$-$C_8$alkyl or $C_4$-$C_8$alkoxy.

$R_6$ and $R_7$, when present, are independently chosen at each occurrence from hydrogen, halogen, $C_1$-$C_4$alkyl, $C_1$-$C_4$alkoxy, and phenyl; or $R_6$ and $R_7$ may be joined to form a 3- to 7-membered cycloalkyl ring.

Also provided herein are compounds and pharmaceutically acceptable salts of Formula IB, which have the same chemical formula and compounds of Formula I, but in which the variables, e.g. z, $A_1$-$A_5$, R, and $R_1$-$R_7$ have the values set forth below.

Within Formula IB z is 0, 1, or 2.

R is hydrogen, methyl, or ethyl.

$A_1$ is nitrogen or $CR_1$; $A_2$ is nitrogen or $CR_2$; $A_3$ is nitrogen or $CR_3$; $A_4$ is nitrogen or $CR_4$; and $A_5$ is nitrogen or $CR_5$; where zero or one of $A_1$, $A_2$, $A_3$, $A_4$, or $A_5$ is nitrogen.

$R_1$, $R_4$, and $R_5$ are each independently hydrogen, hydroxy, amino, halogen, cyano, $C_1$-$C_4$alkyl, $C_1$-$C_4$alkoxy, $C_1$-$C_2$haloalkyl, or $C_1$-$C_2$haloalkoxy;

When z is 0; one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is (a) $C_3$-$C_6$alkyl or $C_3$-$C_6$alkoxy, each of which is substituted with at least one $C_1$-$C_4$alkoxy or mono- or di-$C_1$-$C_4$alkylamino;

(b) $C_4$-$C_8$alkoxycarbonyl;

(c) (phenyl)ethyl, (phenyl)$C_1$-$C_2$alkoxy, (phenyl)$C_1$-$C_2$alkylamino, (phenylamino)$C_1$-$C_2$alkyl, (phenoxy)$C_1$-$C_2$alkyl, or (pyridyl)L-, where L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl-;

(d) ($C_5$-$C_7$cycloalkyl)L- or (heterocycloalkyl)L-, each of which is optionally bridged and optionally fused to a 6-membered carbocyclic ring or a 6-membered heterocyclic ring containing 1 or 2 heteroatoms independently chosen from N, O, and S; or (e) (phenyl)L- or (pyridyl)L-, each of which is fused to a 5- or 6-membered heterocycloalkyl group containing 1 or 2 oxygen atoms.

wherein each of (a), (b), (c), (d), and (e), is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, phenyl, and pyridyl.

Or one of $R_2$ and $R_3$ is halogen, $C_1$-$C_2$alkoxy, $C_1$-$C_2$haloalkyl, or $C_1$-$C_2$haloalkoxy, and the other is cyclohexyl, piperidinyl, $C_5$-$C_8$alkyl, $C_5$-$C_8$alkenyl $C_5$-$C_8$alkynyl, or $C_4$-$C_8$alkoxy.

When z is 1 or 2, provided that $R_2$ is not benzyloxy or cyclopentyloxy when $R_3$ is methoxy, one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is (i) $C_3$-$C_6$alkyl or $C_3$-$C_6$alkoxy, substituted with $C_1$-$C_4$alkoxy or mono- or di-$C_1$-$C_4$alkylamino;

(ii) $C_4$-$C_8$alkoxycarbonyl, $C_5$-$C_8$alkenyl, or $C_5$-$C_8$alkynyl;

(iii) (phenyl)L- or (pyridyl)L-, each of which is optionally fused to a 6-membered carbocyclic ring or a 5- or 6-membered heterocyclic ring containing 1 or 2 heteroatoms independently chosen from N, O, and S; or (iv) ($C_5$-$C_7$cycloalkyl)L- or (heterocycloalkyl)L-, each of which is optionally bridged and each of which is optionally fused to a 6-membered carbocyclic ring or 6-membered heterocyclic ring containing 1 or 2 heteroatoms independently chosen from N, O, and S.

Wherein each of (i), (ii), (iii), and (iv), is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, phenyl, and pyridyl; or one of $R_2$ and $R_3$ is halogen, $C_1$-$C_2$alkoxy, $C_1$-$C_2$haloalkyl, or $C_1$-$C_2$haloalkoxy, and the other is $C_5$-$C_8$alkyl, or $C_4$-$C_8$alkoxy.

$R_6$ and $R_7$, when present, are independently chosen from hydrogen, halogen, $C_1$-$C_4$alkyl, $C_1$-$C_4$alkoxy, and phenyl; $R_6$ and $R_7$ may be joined to form a 3- to 7-membered cycloalkyl ring.

Further provided herein are compounds and pharmaceutically acceptable salts of Formula I, Formula IA and Formula IB in which one or more of the following conditions are met:

(1) R is hydrogen.

(2) $R_1$, $R_4$, and $R_5$ are each independently hydrogen, chloro, fluoro, cyano, methyl, or ethyl.

(3) $R_1$, $R_4$, and $R_5$ are all hydrogen.

(4) $A_1$ is $CR_1$, $A_2$ is $CR_2$, $A_3$ is $CR_3$, $A_4$ is $CR_4$, and $A_5$ is $CR_5$, e.g. Compounds and salts of Formula 2 are provided herein.

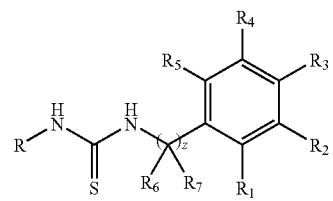

Formula 2

(5) $A_1$ is nitrogen, $A_2$ is $CR_2$, $A_3$ is $CR_3$, $A_4$ is $CR_4$, and $A_5$ is $CR_5$, e.g. Compounds and salts of Formula 3 are provided herein.

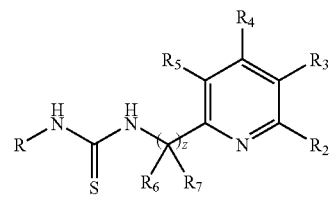

Formula 3

(6) $A_1$ is $CR_1$, $A_2$ is nitrogen $A_3$ is $CR_3$, $A_4$ is $CR_4$, and $A_5$ is $CR_5$, e.g. Compounds and salts of Formula 4 are provided herein.

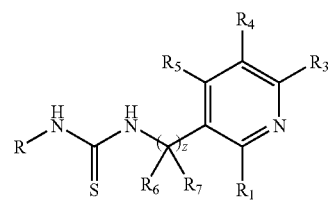

Formula 4

(7) $A_1$ is $CR_1$, $A_2$ is $CR_2$, $A_3$ is nitrogen, $A_4$ is $CR_4$, and $A_5$ is $CR_5$, e.g. Compounds and salts of Formula 5 are provided herein

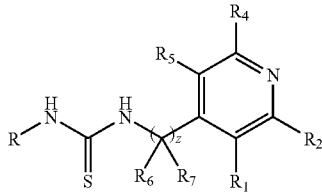

Formula 5

(8) $A_1$ is $CR_1$, $A_2$ is $CR_2$, $A_3$ is $CR_3$, $A_4$ is nitrogen, and $A_5$ is $CR_5$, e.g. Compounds and salts of Formula 6 are provided herein

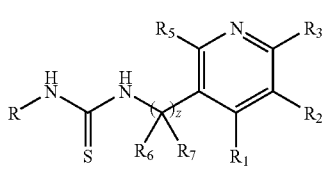

Formula 6

(9) The variable z is 0. One of $R_2$ and $R_3$ is hydrogen, hydroxy, amino, halogen, $C_1$-$C_2$alkyl, $C_1$-$C_2$alkoxy, $C_1$-$C_2$haloalkyl, or $C_1$-$C_2$haloalkoxy; and the other of $R_2$ and $R_3$ is $C_3$-$C_6$alkyl or $C_3$-$C_6$alkoxy, each of which is substituted with $C_1$-$C_4$alkoxy or mono- or di-$C_1$-$C_4$alkylamino.

(10) The variable z is 0, one of $R_2$ and $R_3$ is hydrogen, hydroxy, amino, halogen, $C_1$-$C_2$alkyl, $C_1$-$C_2$alkoxy, $C_1$-$C_2$haloalkyl, or $C_1$-$C_2$haloalkoxy; and the other of $R_2$ and $R_3$ is $C_4$-$C_8$alkoxycarbonyl.

(11) The variable z is 0 and one of $R_2$ and $R_3$ is hydrogen, hydroxy, amino, halogen, $C_1$-$C_2$alkyl, $C_1$-$C_2$alkoxy, $C_1$-$C_2$haloalkyl, or $C_1$-$C_2$haloalkoxy; and the other of $R_2$ and $R_3$ is (phenyl)$C_1$-$C_2$alkoxy, (phenyl)$C_1$-$C_2$alkylamino, (phenylamino)$C_1$-$C_2$alkyl, (phenoxy)$C_1$-$C_2$alkyl, and (pyridyl)L-; each of which is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_4$alkanoyl, $C_1$-$C_6$alkoxycarbonyl, $C_1$-$C_2$haloalkyl, $C_1$-$C_2$haloalkoxy, phenyl, and pyridyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl-.

(12) The variable z is 0 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (phenyl)$C_1$-$C_2$alkoxy, (phenyl)$C_1$-$C_2$alkylamino, (phenylamino)$C_1$-$C_2$alkyl, (phenoxy)$C_1$-$C_2$alkyl, and (pyridyl)L-; each of which is substituted with 0 to 3 substituents independently chosen from cyano, halogen, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl-.

(13) The variable z is 0 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (phenyl)$C_1$-$C_2$alkoxy, (phenyl)$C_1$-$C_2$alkylamino, (phenylamino)$C_1$-$C_2$alkyl, (phenoxy)$C_1$-$C_2$alkyl, and (pyridyl)L-; each of which is substituted with 0 to 3 substituents independently chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Wherein L is $C_0$-$C_2$alkyl, $C_0$-$C_2$alkoxy, or $C_0$-$C_2$alkylamino.

(14) The variable z is 0; and one of $R_2$ and $R_3$ is hydrogen, hydroxy, amino, halogen, $C_1$-$C_2$alkyl, $C_1$-$C_2$alkoxy, $C_1$-$C_2$haloalkyl, or $C_1$-$C_2$haloalkoxy. The other of $R_2$ and $R_3$ is (cyclopentyl)L- or (pyrrolidinyl)L-, each of which is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl) amino, $C_2$-$C_4$alkanoyl, $C_1$-$C_6$alkoxycarbonyl, $C_1$-$C_2$haloalkyl, $C_1$-$C_2$haloalkoxy, phenyl, and pyridyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl.

(15) The variable z is 0 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (cyclopentyl)L- or (pyrrolidinyl)L-; each of which is substituted with 0 to 3 substituents independently chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Where L is $C_0$-$C_2$alkyl, $C_0$-$C_2$alkoxy, or $C_0$-$C_2$alkylamino.

(16) The variable z is 0 and one of $R_2$ and $R_3$ is hydrogen, amino, halogen, $C_1$-$C_2$alkyl, $C_1$-$C_2$alkoxy, $C_1$-$C_2$haloalkyl, or $C_1$-$C_2$haloalkoxy. The other of $R_2$ and $R_3$ is (e) (cyclohexyl)$C_0$-$C_2$alkyl, (cyclopentyl)$C_0$-$C_2$alkyl, (piperidinyl)$C_0$-$C_2$alkyl or (pyrrolidinyl)$C_0$-$C_2$alkyl, each of which is fused to a 6-membered carbocyclic ring or 6-membered heterocyclic ring containing 1 or 2 heteroatoms independently chosen from N, O, and S; each of which (e) is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl) amino, $C_2$-$C_4$alkanoyl, $C_1$-$C_6$alkoxycarbonyl, $C_1$-$C_2$haloalkyl, $C_1$-$C_2$haloalkoxy, phenyl, and pyridyl.

(17) The variable z is 0; and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (e) (cyclohexyl)$C_0$-$C_2$alkyl, (cyclopentyl)$C_0$-$C_2$alkyl, (piperidinyl)$C_0$-$C_2$alkyl or (pyrrolidinyl)$C_0$-$C_2$alkyl, each of which is fused to a phenyl, cyclohexenyl, cyclohexyl, piperidinyl, or pyridyl ring; each of which (e) is substituted with 0 to 3 substituents independently chosen from chosen from cyano, halogen, $C_1$-$C_4$alkyl, $C_1$-$C_4$alkoxy, $C_1$-$C_2$haloalkyl, $C_1$-$C_2$haloalkoxy, and phenyl.

(18) The variable z is 0; and one of $R_2$ and $R_3$ is hydrogen, hydroxy, amino, halogen, $C_1$-$C_2$alkyl, $C_1$-$C_2$alkoxy, $C_1$-$C_2$haloalkyl, or $C_1$-$C_2$haloalkoxy. The other of $R_2$ and $R_3$ is (phenyl)$C_0$-$C_2$alkyl or (pyridyl)$C_0$-$C_2$alkyl, each of which is fused to a 5- or 6-membered heterocycloalkyl group containing 1 or 2 oxygen atoms, each of which is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_4$alkanoyl, $C_1$-$C_6$alkoxycarbonyl, $C_1$-$C_2$haloalkyl, $C_1$-$C_2$haloalkoxy, phenyl, and pyridyl. In some preferred compounds and salts of Formula I the 5- or 6-membered heterocycloalkyl group contains 2 oxygen atoms.

(19) The variable z is 0 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is

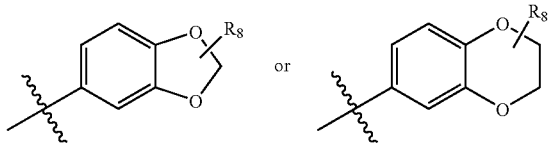

wherein $R_8$ represents 0 to 2 substituents independently chosen from halogen, $C_1$-$C_2$alkyl, $C_1$-$C_2$alkoxy, trifluoromethyl, $C_1$-$C_2$trifluoromethoxy, and phenyl.

(20) The variable z is 0 and one of $R_2$ and $R_3$ is hydrogen, hydroxy, amino, halogen, $C_1$-$C_2$alkyl, $C_1$-$C_2$alkoxy, $C_1$-$C_2$haloalkyl, or $C_1$-$C_2$haloalkoxy. The other of $R_2$ and $R_3$ is cyclohexyl, piperidinyl, bridged cyclohexyl, or bridged piperidinyl, each of which is substituted with at least one substituent chosen from $C_2$-$C_6$alkoxycarbonyl, phenyl, pyridyl, $C_4$-$C_8$ alkyl, and $C_4$-$C_8$alkoxy; and further substituted with 0 to 3 substituents independently chosen from, hydroxy, amino, cyano, halogen, $C_1$-$C_6$alkyl, $C_1$-$C_6$alkoxy, $C_1$-$C_2$haloalkyl, and $C_1$-$C_2$haloalkoxy.

(21) One of $R_2$ and $R_3$ is hydrogen, halogen, $C_1$-$C_2$alkyl, $C_1$-$C_2$alkoxy, trifluoromethyl, or trifluoromethoxy; and the other of $R_2$ and $R_3$ is cyclohexyl, piperidinyl, bridged cyclohexyl, or bridged piperidinyl, each of which is substituted with 1 or 2 substituents independently chosen from $C_2$-$C_6$alkoxycarbonyl, phenyl, pyridyl, $C_4$-$C_8$ alkyl, and $C_4$-$C_8$alkoxy.

(22) One of $R_2$ and $R_3$ is halogen, $C_1$-$C_2$alkyl, $C_1$-$C_2$alkoxy, $C_1$-$C_2$haloalkyl, or $C_1$-$C_2$haloalkoxy, and the other is cyclohexyl, piperidinyl, $C_5$-$C_8$alkyl, $C_5$-$C_8$alkenyl $C_5$-$C_8$alkynyl, or $C_4$-$C_8$alkoxy.

(23) One of $R_2$ and $R_3$ is chloro, fluoro, methoxy, trifluoromethyl, or trifluoromethoxy, and the other is cyclohexyl, piperidinyl, $C_5$-$C_8$alkyl, or $C_4$-$C_8$alkoxy.

(24) The variable z is 1.

(25) The variable z is 2.

(26) The variable z is 1 or 2 and one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy. The other of $R_2$ and $R_3$ is $C_3$-$C_6$alkyl or $C_3$-$C_6$alkoxy, substituted with one $C_1$-$C_4$alkoxy or mono- or di-$C_1$-$C_4$alkylamino.

(27) The variable z is 1 or 2 and one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is $C_4$-$C_8$alkoxycarbonyl, $C_5$-$C_8$alkenyl, or $C_5$-$C_8$alkynyl.

(28) The variable z is 1 or 2 and one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy. The other of $R_2$ and $R_3$ is (phenyl)L- or (pyridyl)L-, each of which is optionally fused to a 6-membered carbocyclic ring or a 5- or 6-membered heterocyclic ring containing 1 or 2 heteroatoms independently chosen from N, O, and S. Each of which (phenyl)L- or (pyridyl)L- is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, phenyl, and pyridyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl.

(29) The variable z is 1 or 2 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (phenyl)L- or (pyridyl)L-; each of which is substituted with 0 to 3 substituents independently chosen from chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl. In certain preferred compounds and salts of Formula I L is $C_0$-$C_2$alkyl, $C_0$-$C_2$alkoxy, or $C_0$-$C_2$alkylamino.

(30) The variable z is 1 or 2 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (phenyl)L- or (pyridyl)L-; each of which is fused to a 6-membered carbocyclic ring or a 5- or 6-membered heterocyclic ring containing 1 or 2 heteroatoms independently chosen from N, O, and S. Each of which (phenyl)L- or (pyridyl)L- is substituted with 0 to 3 substituents independently chosen from chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl. In certain preferred compounds and salts of Formula I L is $C_0$-$C_2$alkyl, $C_0$-$C_2$alkoxy, or $C_0$-$C_2$alkylamino.

(31) The variable z is 1 or 2 and one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy. The other of $R_2$ and $R_3$ is ($C_5$-$C_7$cycloalkyl)L- or (heterocycloalkyl)L-, each of which is optionally bridged and each of which is optionally fused to a 6-membered carbocyclic ring or 6-membered heterocyclic ring containing 1 or 2 heteroatoms independently chosen from N, O, and S.

Each of which ($C_5$-$C_7$cycloalkyl)L- or (heterocycloalkyl)L-, is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, phenyl, and pyridyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl. In certain preferred compounds and salts of Formula I L is $C_0$-$C_2$alkyl, $C_0$-$C_2$alkoxy, or $C_0$-$C_2$alkylamino.

(32) The variable z is 1 or 2 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (cyclohexyl)L-, (cyclopentyl)L- or (piperidinyl)L-, each of which is optionally bridged and each of which is substituted with 0 to 3 substituents independently chosen from chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl. In certain preferred compounds and salts of Formula I L is $C_0$-$C_2$alkyl, $C_0$-$C_2$alkoxy, or $C_0$-$C_2$alkylamino

(33) The variable z is 1 or 2 and one of $R_2$ and $R_3$ is hydrogen, halogen, $C_1$-$C_2$alkyl, $C_1$-$C_2$alkoxy, trifluoromethyl, or trifluoromethoxy. The other of $R_2$ and $R_3$ is (cyclohexyl)L-, (cyclopentyl)L- or (piperidinyl)L-, each of which is optionally fused to a phenyl, pyridyl, cyclohexyl, cyclohexenyl, or piperidinyl ring.

Each of which is (cyclohexyl)L-, (cyclopentyl)L- or (piperidinyl)L- is substituted with 0 to 3 substituents independently chosen from chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl.

In certain preferred compounds and salts of Formula I L is $C_0$-$C_2$alkyl, $C_0$-$C_2$alkoxy, or $C_0$-$C_2$alkylamino.

(34) The variable z is 1 or 2 and one of $R_2$ and $R_3$ is hydrogen, halogen, $C_1$-$C_2$alkyl, $C_1$-$C_2$alkoxy, trifluoromethyl, or trifluoromethoxy.

The other of $R_2$ and $R_3$ is (cyclohexyl)L-, (cyclopentyl)L- or (piperidinyl)L-, each of which is substituted with 0 to 3 substituents independently chosen from chosen from cyano, halogen, $C_1$-$C_4$alkyl, $C_1$-$C_4$alkoxy, $C_1$-$C_2$haloalkyl, $C_1$-$C_2$haloalkoxy, and phenyl.

Wherein L is $C_0$-$C_3$alkyl, —C(phenyl)$_2$-, $C_0$-$C_2$alkoxy, $C_0$-$C_2$alkylamino, —O—$C_1$-$C_2$alkyl, or —NH—$C_1$-$C_2$alkyl. In certain preferred compounds and salts of Formula I L is $C_0$-$C_2$alkyl, $C_0$-$C_2$alkoxy, or $C_0$-$C_2$alkylamino.

(35) The variable z is 1 or 2 and one of $R_2$ and $R_3$ is halogen, $C_1$-$C_2$alkoxy, $C_1$-$C_2$haloalkyl, or $C_1$-$C_2$haloalkoxy, and the other of $R_2$ and $R_3$ is $C_5$-$C_8$alkyl or $C_4$-$C_8$alkoxy.

(36) $R_6$ and $R_7$, when present, are independently hydrogen, halogen, methyl, or ethyl.

For example, compounds and salts thereof of Formula 7-20 are included herein.

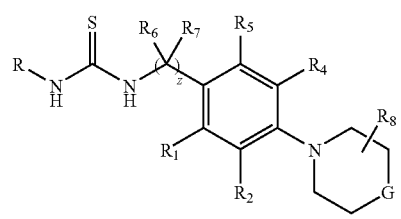

Formula 7

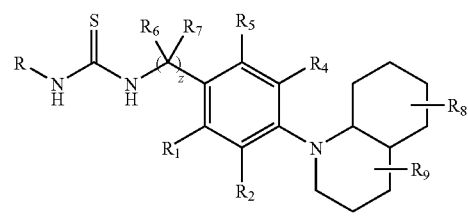

Formula 8

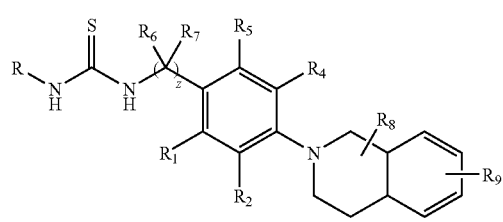

Formula 9

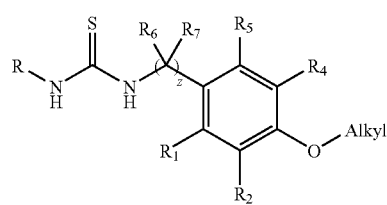

Formula 10

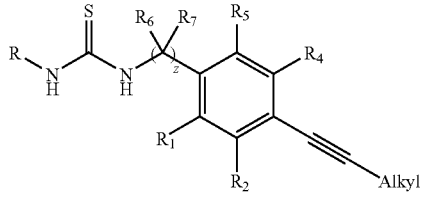

Formula 11

-continued

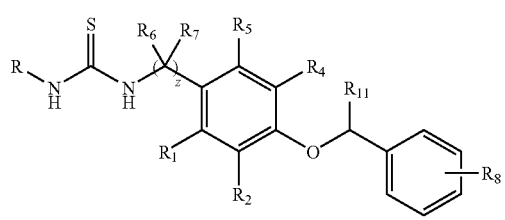

Formula 12

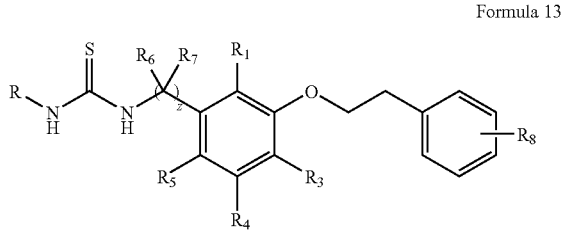

Formula 13

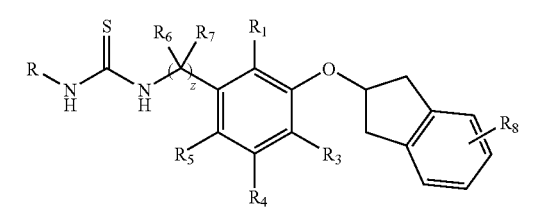

Formula 14

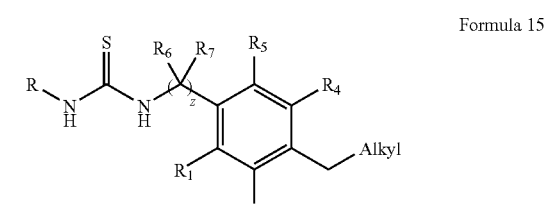

Formula 15

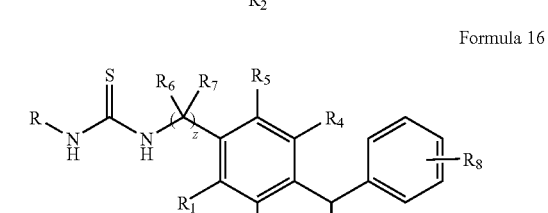

Formula 16

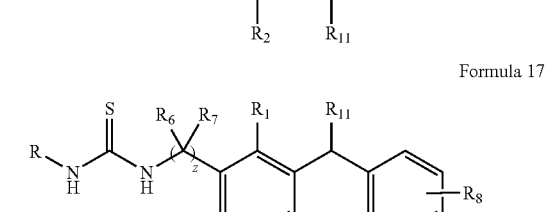

Formula 17

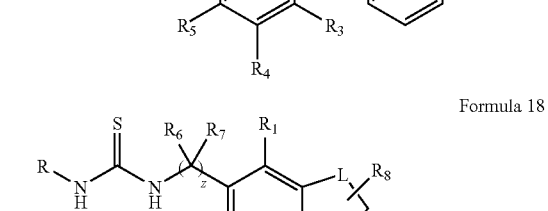

Formula 18

-continued

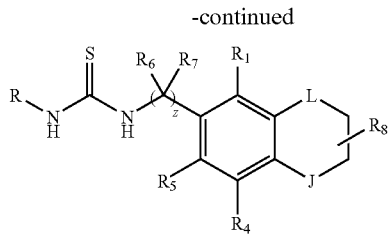
Formula 19

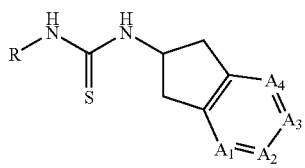
Formula 20

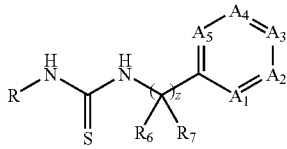
Formula I and the pharmaceutically acceptable salts thereof.

Within Formula IC the variables z, R, $A_1$, $A_2$, $A_3$, $A_4$, $A_5$, $R_6$, and $R_7$ carry the following definitions:

The variable z is 0, 1, 2, 3 or 4.

R is hydrogen, methyl, or ethyl.

$A_1$ is nitrogen or $CR_1$; $A_2$ is nitrogen or $CR_2$; $A_3$ is nitrogen or $CR_3$; $A_4$ is nitrogen or $CR_4$; $A_5$ is nitrogen or $CR_5$; where zero or one of $A_1$, $A_2$, $A_3$, $A_4$, or $A_5$ is nitrogen.

$R_1$, $R_4$, and $R_5$ are each independently hydrogen, hydroxy, amino, halogen, cyano, $C_1$-$C_4$alkyl, $C_1$-$C_4$alkoxy, $C_1$-$C_2$haloalkyl, or $C_1$-$C_2$haloalkoxy.

One of $R_2$ and $R_3$ is chosen from hydrogen, hydroxy, amino, cyano, halogen, $C_1$-$C_6$alkyl, $C_1$-$C_6$alkoxy, $C_1$-$C_2$haloalkyl, and $C_1$-$C_2$haloalkoxy, The other of $R_2$ and $R_3$ is chosen from (a), (b), and (c).

Where (a) is $C_3$-$C_{10}$cycloalkyl optionally fused to a phenyl ring and $C_2$-$C_7$heterocycloalkyl optionally fused to a phenyl or $C_3$-$C_8$ cycloalkyl ring, each of which (a) is substituted with 0 to 3 substituents independently chosen from (i) hydroxy, cyano, amino, —COON, —CONH$_2$, halogen, $C_1$-$C_6$alkyl, $C_1$-$C_6$alkoxy, $C_1$-$C_2$haloalkyl, $C_1$-$C_2$haloalkoxy, mono- and di-$C_1$-$C_6$alkylamino, $C_2$-$C_6$alkanoyl, $C_1$-$C_6$alkoxycarbonyl, $C_1$-$C_6$alkylcarboxamide, and (ii) phenyl($C_0$-$C_4$alkyl) and pyridyl($C_0$-$C_4$alkyl), each of which is substituted with 0 to 3 substituents independently chosen from hydroxy, amino, halogen, $C_1$-$C_4$ alkyl, $C_1$-$C_4$alkoxy, $C_1$-$C_2$haloalkyl, and $C_1$-$C_2$haloalkoxy; and And (b) is X—$R_a$ where X is —(CH$_2$)$_n$NH—, —(CH$_2$)$_n$NR$_{10}$—, —(CH$_2$)$_n$O—, —CH═CH—, or —C≡C—, where n is 0, 1, or 2, and $R_a$ is $C_1$-$C_8$alkyl, $C_2$-$C_8$alkenyl, $C_2$-$C_8$alkynyl, $C_3$-$C_{10}$cycloalkyl($C_0$-$C_4$carbhydryl), $C_2$-$C_7$heterocycloalkyl, aryl($C_0$-$C_6$carbhydryl), heteroaryl($C_0$-$C_6$carbhydryl), indanyl, or tetrahydronaphthyl, each of which is substituted with 0-3 substituents independently chosen from hydroxy, amino, —COOH, —CONH$_2$, halogen, $C_1$-$C_6$alkyl, $C_1$-$C_6$alkoxy, $C_1$-$C_2$haloalkyl, $C_1$-$C_2$haloalkoxy, mono- and di-$C_1$-$C_6$alkylamino, $C_2$-$C_6$alkanoyl, $C_1$-$C_6$alkoxycarbonyl, $C_1$-$C_6$alkylcarboxamide, and phenyl.

$R_{10}$ is $C_1$-$C_6$alkyl, $C_2$-$C_6$alkenyl, $C_2$-$C_6$alkynyl, $C_3$-$C_7$cycloalkyl, $C_3$-$C_7$cycloalkyl($C_1$-$C_4$carbhydryl), or aryl, each of which is substituted with 0 to 3 substituents independently chosen from hydroxy, amino, —COOH, —CONH$_2$, halogen, $C_1$-$C_4$alkyl, $C_1$-$C_4$alkoxy, $C_1$-$C_2$haloalkyl, $C_1$-$C_2$haloalkoxy, and mono- and di-$C_1$-$C_4$alkylamino.

And (c) is Y—$R_b$ where Y is $C_1$-$C_4$alkyl substituted with 0 to 3 substituents independently chosen from halogen, amino, $C_1$-$C_2$alkyl, and $C_1$-$C_2$alkoxy, and $R_b$ is chosen from $C_1$-$C_8$alkyl, $C_2$-$C_8$alkenyl, $C_2$-$C_8$alkynyl, $C_1$-$C_6$alkoxy, mono- or di-($C_1$-$C_6$alkyl)amino, $C_3$-$C_{10}$cycloalkyl($C_0$-$C_4$carbhydryl), $C_2$-$C_7$heterocycloalkyl, aryl($C_0$-$C_6$carbhydryl), heteroaryl($C_0$-$C_6$carbhydryl), indanyl, or tetrahydronaphthyl, each of which is substituted with 0 to 3 substituents independently chosen from hydroxy, amino, —COOH, —CONH$_2$, halogen, $C_1$-$C_6$alkyl, $C_1$-$C_6$alkoxy, $C_1$-$C_2$haloalkyl, $C_1$-$C_2$haloalkoxy, mono- and di-$C_1$-

Within Formulae 7-20, z, R, $R_1$, $R_4$, $R_5$, $R_6$, and $R_7$ may carry any of the definitions set forth herein for these variables. For example, $R_1$ may carry the definition set forth in Formula I, in which $R_1$ is hydrogen, hydroxy, amino, halogen, cyano, $C_1$-$C_4$alkyl, $C_1$-$C_4$alkoxy, $C_1$-$C_2$haloalkyl, or $C_1$-$C_2$haloalkoxy, or $R_1$ may carry the definition set forth in condition (2) in which $R_1$ is hydrogen, chloro, fluoro, cyano, methyl, or ethyl.

G in Formula 7 is NH, CH$_2$, or O.

$R_8$ and $R_9$ each represent 0 to 3 substituents independently chosen from hydroxy, amino, —COOH, —CONH$_2$, halogen, $C_1$-$C_6$alkyl, $C_1$-$C_6$alkoxy, $C_1$-$C_2$haloalkyl, $C_1$-$C_2$haloalkoxy, mono- and di-$C_1$-$C_6$alkylamino, $C_2$-$C_6$alkanoyl, $C_1$-$C_6$alkoxycarbonyl, $C_1$-$C_6$alkylcarboxamide, and phenyl.

The "Alkyl-O—," "Alkyl-C≡C—," or "Alkyl" substituent shown at the $R_3$ position in Formula 10, Formula 11, or Formula 15, respectively, is a straight or branched chain saturated alkyl group of 3 to 9 membered is optionally substituted with 0 to 3 substituents independently chosen from hydroxy, amino, halogen, $C_1$-$C_4$alkoxy, trifluoromethyl, trifluoromethoxy, and mono- and di-$C_1$-$C_4$alkylamino $R_{11}$ is hydrogen or methyl.

In both Formula 18 and Formula 19 one of J and L is oxygen and the other is NH, CH$_2$, S, or O. In certain preferred embodiments $R_2$ is chosen from halogen, methoxy, trifluoromethyl, and trifluoromethoxy. In some preferred embodiments of Formula 17 $R_3$ is halogen, methoxy, trifluoromethyl, and trifluoromethoxy.

The invention also includes compounds and salts of Formula I in which compounds and salts of Formula I in which the variables R, $R_1$, $R_4$, and $R_5$ carry the definitions set forth above and $R_2$ and $R_3$ are joined to form a 5-6 membered ring that contains 1 or 2 oxygen atoms and is substituted with 0-2 substituents independently chosen from chloro, fluoro, $C_1$-$C_2$ alkyl, $C_1$-$C_2$alkoxy, trifluoromethyl, trifluoromethoxy, and phenyl.

Any of the values given herein for the variables shown in Formula I, or any of the subformulae thereof, e.g. R, $R_1$-$R_7$, z, $A_1$-$A_5$ may be combined so long as a stable compound of Formula I results.

In another embodiment compounds and pharmaceutically acceptable salts of Formula IC, which have the same chemical formula and compounds of Formula I, but in which the variables, e.g. z, $A_1$-$A_5$, R, and $R_1$-$R_7$ have the values set forth below are also provided herein $C_6$alkylamino, $C_2$-$C_6$alkanoyl, $C_1$-$C_6$alkoxycarbonyl, $C_1$-$C_6$alkylcarboxamide, and phenyl.

Alternatively $R_2$ and $R_3$ are joined to form a 5-7 membered ring that contains 0, 1, or 2 heteroatoms independently chosen from nitrogen, oxygen, and sulfur, and substituted with 0 to 3 substituents independently chosen from hydroxy, amino, halogen, $C_1$-$C_4$ alkyl, $C_1$-$C_4$alkoxy, $C_1$-$C_2$haloalkyl, $C_1$-$C_2$haloalkoxy, phenyl, and bi-phenyl.

$R_6$ and $R_7$, when present, are independently chosen at each occurrence from hydrogen, halogen, $C_1$-$C_4$alkyl, $C_1$-$C_4$alkoxy, or phenyl. Preferably $R_6$ and $R_7$, when present, are both hydrogen.

Certain compounds of Formula I and the subformulae thereof, Formula IA, Formula IB, Formula IC, and Formula 2-Formula 20, exhibit antiviral activity, especially anti-HCV activity. Particular compounds of Formula I disclosed herein are inhibitors of viral replication, especially HCV replication. Compounds of Formula I disclosed herein are potent inhibitors of the HCV replicon in the standard HCV replicon assay disclosed in Example 9, which follows. Without wishing to be bound to any particular theory, it is believed that the anti-HCV activity of compounds of Formula I is due to their inhibit replication of the HCV replicon. Preferred substituted aryl thioureas of Formula I exhibit an $EC_{50}$ of about 10 micromolar or less, or more preferably an $EC_{50}$ of about 1 micromolar or less; or an $EC_{50}$ of about 500 nanomolar or less in an HCV replicon assay.

Preferred compounds of Formula I will have certain pharmacological properties. Such properties include, but are not limited to oral bioavailability, low toxicity, low serum protein binding and desirable in vitro and in vivo half-lifes.

Pharmaceutical Preparations

Compounds and salts of the invention can be administered as the neat chemical, but are preferably administered as a pharmaceutical composition or formulation. Accordingly, the invention provides pharmaceutical formulations comprising a compound or pharmaceutically acceptable salt of Formula 1, together with one or more pharmaceutically acceptable carriers, excipients, adjuvant, diluent, or other ingredients.

One embodiment pertains to pharmaceutical composition comprising a compound or pharmaceutically acceptable salt thereof of Formula I together with at least one pharmaceutically acceptable carrier, diluent, or excipient, wherein the composition is formulated as an injectable fluid, an aerosol, a cream, a gel, a tablet, a pill, a capsule, a syrup, ophthalmic solution, or a transdermal patch.

In addition to one or more compounds of the invention, pharmaceutical compositions of the invention may contain a pharmaceutically acceptable carrier, one or more compatible solid or liquid filler diluents or encapsulating substances, which are suitable for administration to a patient. Carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, and polyethylene glycol; alginic acid; emulsifiers, such as the TWEENS; bioavailability enhancers, such as lauroyl macroglycerides, including GELUCIRE, wetting agents, such sodium lauryl sulfate; coloring agents; flavoring agents; tableting agents, stabilizers; antioxidants; preservatives; pyrogen-free water; isotonic saline; and phosphate buffer solutions.

Optional active agents may be included in a pharmaceutical composition, which do not substantially interfere with the activity of the compounds of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of the invention, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder, or condition treated and may be empirically determined.

Compounds of general the invention may be administered orally, topically, parenterally, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. Oral formulations contain between 0.1 and 99% of a compound of the invention and usually at least about 5% (weight %) of a compound of the present invention. Some embodiments contain from about 25% to about 50% or from 5% to 75% of a compound of invention.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Orally Administered Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions provided herein may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The compound or compounds of the invention, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least about 90% by weight of the total composition. Preferred carriers for parenteral administration include propylene glycol, ethyl oleate, pyrrolidone, ethanol, and sesame oil.

Suppositories

Compounds of the invention may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye or for intracisternal or intraspinal application. Topical compositions of the present invention may be in any form including, for example, solutions, creams, ointments, gels, lotions, milks, cleansers, moisturizers, sprays, skin patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, isobutane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions provided herein may also optionally comprise an activity enhancer. The activity enhancer can be chosen from a wide variety of molecules that function in different ways to enhance antimicrobial effects of compounds described herein. Particular classes of activity enhancers include skin penetration enhancers and absorption enhancers.

Pharmaceutical compositions may also contain additional active agents can be chosen from a wide variety of molecules, which can function in different ways to enhance the antimicrobial or therapeutic effects of a compound of the present invention. These optional other active agents, when present, are typically employed in the compositions described herein at a level ranging from about 0.01% to about 15%. Some embodiments contain from about 0.1% to about 10% by weight of the composition. Other embodiments contain from about 0.5% to about 5% by weight of the composition.

Packaged Formulations

Packaged pharmaceutical formulations are included herein. Such packaged formulations include a pharmaceutical composition containing one or more compounds or salts thereof of Formula I in a container and optionally contain instructions for using the composition to treat an animal (typically a human patient) suffering from a microorganism infection or disorder or prevent a microorganism infection in a patient.

One embodiment pertains to a packaged pharmaceutical composition comprising a pharmaceutical composition of Formula I in a container and further comprising instructions for using the composition to treat a patient suffering from Hepatitis C infection.

The invention includes providing prescribing information, for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of the invention can be administered alone, as mixtures, or in combination with other active agents.

Methods of Treatment

The invention includes methods of treating viral infections, particularly HCV infections, by administering an effective amount of one or more compounds of Formula 1 to patient suffering from a viral infection. An effective amount of a compound of Formula 1 may be an amount sufficient to reduce the symptoms of viral infection. Alternatively an effective amount of a compound of Formula 1 may be an amount sufficient to significantly reduce the amount of virus or viral antibodies detectable in a patient's tissues or bodily fluids.

Methods of treatment include administering an amount of a compound of Formula 1 sufficient to reduce or relieve the jaundice, fatigue, dark urine, abdominal pain, loss of appetite, and nausea associated with HCV infection.

Compounds of Formula 1 are thought to ameliorate the HCV disease process by virtue of their inhibition of the replication of the Hepatitis C virus. The compounds provided herein may be virucidal, in that they actually kill the active virus, in addition to independently inhibiting viral replication. The provided compounds may also function through mechanisms that involve a combination of virucidal activity and inhibition of replication.

Methods of treatment encompassed by the invention include administering a compound of Formula 1 as the sole active and administering a compound of Formula 1 together with one or more other active agents, such another antiviral agent, particularly an anti-viral agent effective against HCV infection. The invention includes administering one or more compounds of Formula 1 together with Peg-interferon, Peg-interferon alpha 2b, Ribavarin, natural interferon, Albuferon, interferon beta-1a, IL-10, interferon gamma-1b, AMANTADINE, or ZADAXIM.

Methods of treatment also include inhibiting HCV replication in vivo, in a patient infected with HCV, by administering a sufficient concentration of a compound of Formula 1 to inhibit HCV replicon replication in vitro. By "sufficient concentration" of a compound administered to the patient is meant the concentration of the compound available in the patient's system to combat the infection. Such a concentration by be ascertained experimentally, for example by assaying blood concentration of the compound, or theoretically, by calculating bioavailability.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Synthesis of Compounds

An illustration of the preparation of compounds of the present invention is given in Scheme 1, which depicts a general method for preparation of compound of this invention. Thos having skill in the art will recognize that the starting material may be varied and additional steps employed to produce compound encompassed by the present invention. Within Scheme 1 and Example 1, which follow, the variables, R, $R_1$, $R_2$, $R_3$, $R_4$, and $R_5$ are carry the definitions set forth above. SCHEME 1. Preparation of Substituted Arylthioureas

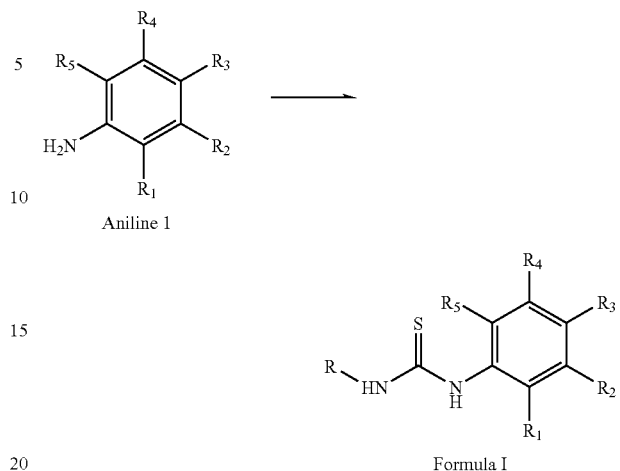

In Scheme 1, an appropriately substituted aniline (Aniline 1) is reacted with appropriate reagent to provide a compound of Formula I. Aniline 1 may be prepared by synthetic methods known to those skilled in the art of organic chemical synthesis. The reagents used to convert the aniline functionality to a thiourea include, but are not limited to alkaline thiocyanates, thiocarbonyl di-imidazole and base followed by treatment with an ammonia source, or thiophosgene and base follow by treatment with an ammonia source.

EXAMPLES

Example 1

Preparation of 1-(3-Benzyloxy)Phenylthiourea (Compound 1)

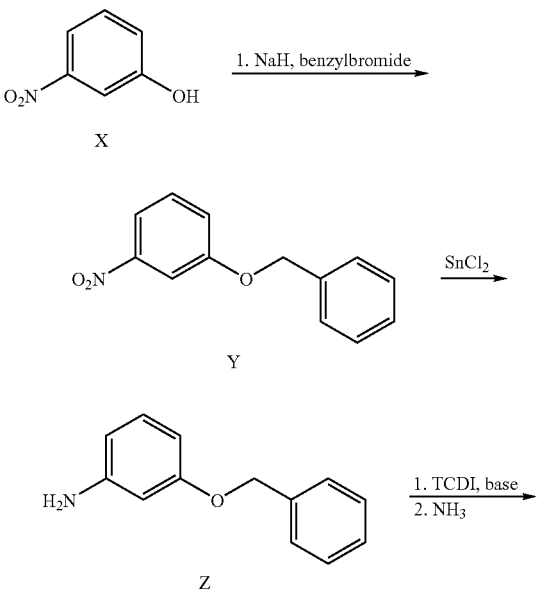

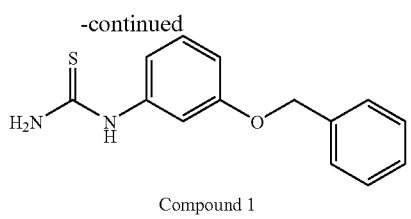

Compound 1

3-Nitrophenol (X) is converted to ether (Y) by sequential treatment with sodium hydride and benzylbromide. Reduction of the aniline with tin chloride provides aniline (Z). In certain circumstances the reduction may be accomplished using a hydrogen/Pd catalyst system when the substituent on the aryl group does not include an aryl group.

The final product, Compound 1 is obtained by treatment of Z with thiocarbonyl di-imidazole followed by ammonia. 3-Benzyloxyaniline (5 g, 25 mmol) is added dropwise over a one minute period to 4.94 g (27.6 mmol) thiocabonyl di-imidazole in methylene chloride (150 ml). The resulting mixture is stirred at room temperature overnight. An additional 400 mg thiocarbonyl di-imidazole (TCDI) is added and the reaction is continued for 2 hours more. The reaction is diluted with hexane and filtered through silica. Concentration provides 5.1 g of the desired 3-benzyloxyphenyl isothiocyanate.

A portion of this isothiocyanate (50 mg, 0.21 mmol) in 1 ml methylene chloride is mixed with 0.5 ml of 2 M ammonia in methanol. After 30 minutes the reaction is concentrated to provide Compound 1 in quantitative yield.

Alternatively thiocarbonyl di-imidazole (1.1 mmol, 196 mg) is added to a solution of 3-benzyloxyaniline (1 mmol, 199 mg) in dichloromethane (5 mL). The reaction is stirred at room temperature until the aniline is consumed, about 1 hour. A solution of methanolic ammonia (2 M, 2 mL) is added and the stirring continued for 2 hours. Solvent is evaporated and the residue purified by chromatography on silica gel to give 150 mg of (3-benzyloxyphenyl)thiourea.

$^1$NMR (CDCl3) □: 5.08 (s, 2H), 6.03 (brs, 2H), 6.8 (m, 2H), 6.93 (m, 1H), 7.3-7.47 (m, 6H), 7.82 (brs, 1H). MS (APCI): M$^+$+1=259.

Example 2

Additional Compounds of the Invention

The following compounds are made by the methods disclosed in Scheme 1 and further illustrated in Example 1. Those of ordinary skill in the art will recognize that the procedures and starting materials may need to be modified slightly in order to obtain the compounds disclosed herein.

1-(4-Cyclohexyl-phenyl)-thiourea (Compound 2)

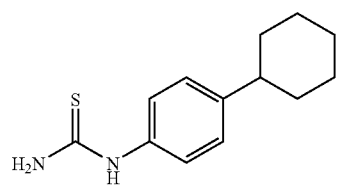

$^1$H NMR (300 MHz, CDCl3) δ 8.04 (br s, 1H, NH), 7.28-7.25 (m, 2H, Aryl H) 7 17-7 14 (m, 2H, Aryl H), 6.11 (br s, 2H, NH$_2$), 2.51 (m, 1H, CH), 1.88-1.74 (m, 5H cyclohexyl) 1.48-1.22 (m, 5H, cyclohexyl). MS (APCI) m/z 235 [M+H]+.

1-(3-Phenoxy-phenyl)-thiourea (Compound 3)

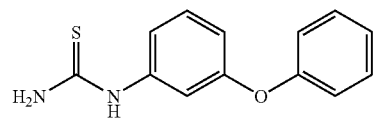

$^1$H NMR (300 MHz, CDCl$_3$) δ 8.46 (br s, 1H, NH), 7.41-6.84 (m, 9H, Aryl H), 6.34 (br s, 2H, NH$_2$). MS (APCI) m/z 245 [M+H]+.

1-(4-Butyloxycarbonyl-phenyl)-thiourea (Compound 4)

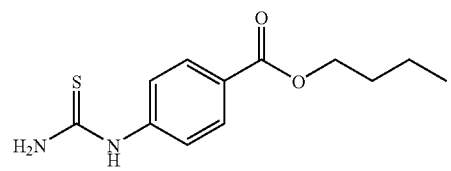

$^1$H NMR (300 MHz, CDCl$_3$) δ 9.14 (s, 1H, NH), 8.07 (d, J=7.5 Hz, 2H, Aryl H), 7.34 (d, J=7.5 Hz, 2H, Aryl H), 6.65 (br s, 2H, NH$_2$), 4.30 (t, J=6.3 Hz, 2H, COCH$_2$), 1.74 (m, 2H, CH$_2$), 1.46 (m, 2H, CH$_2$), 0.97 (t, J=6.0 Hz, 3H, CH$_3$). MS (APCI) m/z 253 [M+H]+.

1-(3-Benzyl-phenyl)-thiourea (Compound 5)

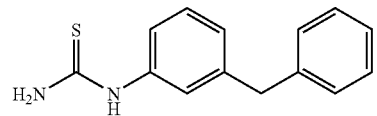

MS (APCI) m/z 243 [M+H]+.

1-(4-Pentyloxy-phenyl)-thiourea (Compound 6)

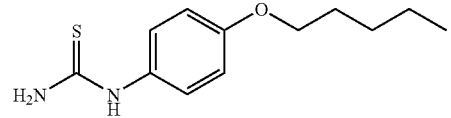

$^1$H NMR (300 MHz, CDCJ$_3$) δ 7.92 (s, 1H, NH), 7.15 (d, J=8.4 Hz, 2H, Aryl H), 6.92 (d, J=8.4 Hz, 2H, Aryl H), 3.95 (t, J=6.6 Hz, 2H, OCH$_2$), 1.82-1.77 (m, 2H, CH$_2$), 1.44-1.38 (m, 4H, (CH$_2$)$_2$), 0.94 (t, J=7.2 Hz, 3H, CH$_3$). MS (APCI) m/z 239 [M+H]+.

1-(4-Pentyl-phenyl)-thiourea (Compound 7)

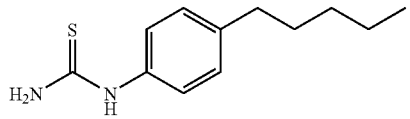

$^1$H NMR (300 MHz, CDCl$_3$) δ 7.99 (br s, 1H, NH), 7.24 (d, J=8.4 Hz, 2H), 7.13 (d, J=8.4 Hz, 2H), 6.09 (br s, 2H, NH$_2$), 2.61 (t, J=7.8 Hz, 2H, CH$_2$), 1.66-1.56 (m, 2H, CH$_2$), 1.38-1.28 (m, 4H, (CH$_2$)$_2$), 0.90 (t, J=6.9 Hz, 3H, CH$_3$). MS (APCI) m/z 223 [M+H]+.

1-(4-Cyclohexylmethyloxy-phenyl)-thiourea (Compound 8)

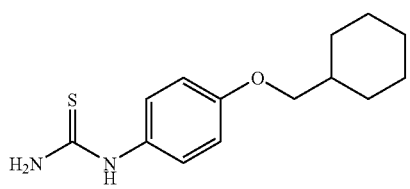

MS (APCI) m/z 265 [M+H]+.

1-(3-Butoxy-phenyl)-thiourea (Compound 9)

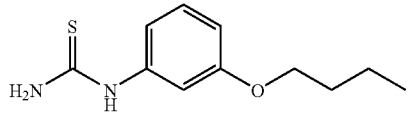

$^1$H NMR (Acetone-d6): 9.10 (s, 1H), 7.25 (t, J=8 Hz, 1H), 7.11 (s, 1H), 7.04 (s, broad, 1H), 6.92 (m, 1H), 6.74 (m, 1H), 4.02 (q, J=9 Hz, 2H), 2.05 (m, 1H), 1.76 (m, 2H), 1.50 (m, 2H) and 0.99 (t, J=8 Hz, 3H) MS: 225.10 (M+1)

1-(4-(3-(dimethylamino)propoxy)phenyl)thiourea (Compound 10)

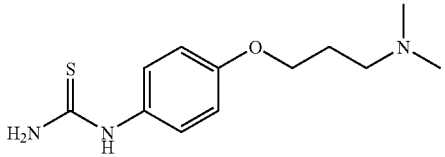

$^1$H NMR (DMSO-d6): 9.48 (s, 1H), 7.38 (s, broad, 1H), 7.22 (d, J=6 Hz, 2H), 6.88 (d, J=6 Hz, 2H), 3.99 (t, J=7.5 Hz, 2H), 2.54 (t, J=9 Hz, 2H), 2.21 (s, 6H) and 1.85 (m, 2H)

1-[3-Fluoro-(4-(3-dimethylaminopropyloxy)phenyl)]thiourea (Compound 11)

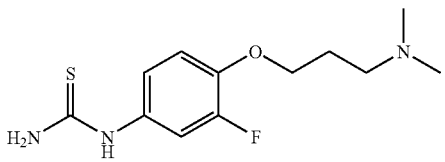

$^1$H NMR (MeOD-d4): 7.12 (m, 3H), 4.12 (t, J=9 Hz, 2H), 2.59 (m, 2H), 2.32 (s, 6H) and 2.02 (m, 2H) MS: 272.4 (M+1)

1-(3-Fluoro-(4-Pentyloxy)-phenyl)-thiourea (Compound 12)

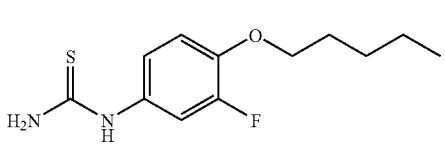

$^1$H NMR (CDCl3): 8.51 (s, 1H), 6.95 (m, 3H), 6.27 (s, broad, 1H), 4.04 (t, J=8 Hz, 2H), 1.82 (m, 2H), 1.43 (m, 4H) and 0.93 (t, J=9 Hz, 3H) MS: 257.0 (M+1)

| CPD # | STRUCTURE | NAME |
|---|---|---|
| 13 | 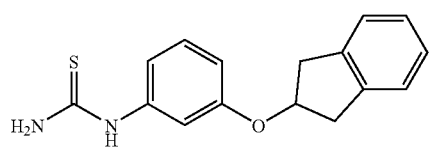 | 1-(3-(indan-2-yloxy)phenyl)thiourea |

| CPD # | STRUCTURE | NAME |
|---|---|---|
| 14 | 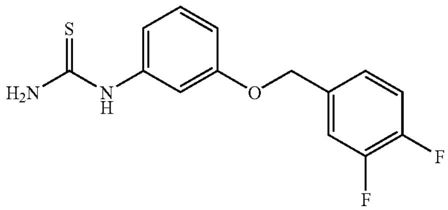 | 1-(3-(3,4-difluorobenzyloxy)phenyl)thiourea |
| 15 | 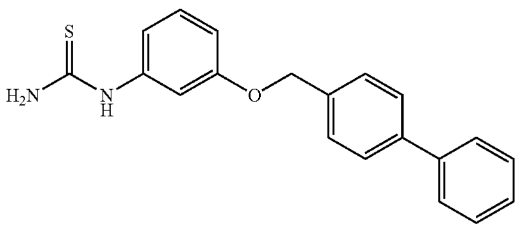 | 1-(3-(4-phenylbenzyloxy)phenyl)thiourea |
| 16 | 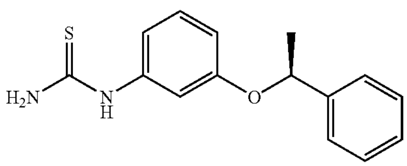 | 1-(3-((S)-1-phenylethoxy)phenyl)thiourea |
| 17 | 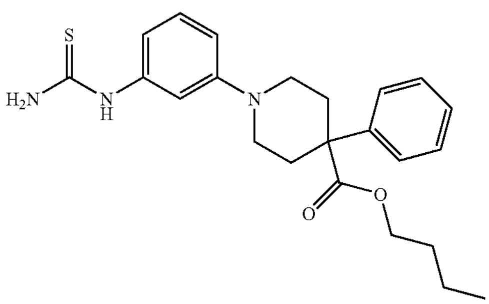 | butyl 4-phenyl-1-(3-thioureidophenyl)piperidine-4-carboxylate |
| 18 | 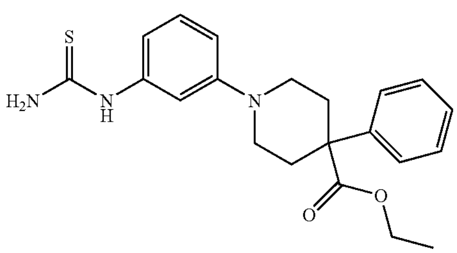 | ethyl 4-phenyl-1-(3-thioureidophenyl)piperidine-4-carboxylate |
| 19 | 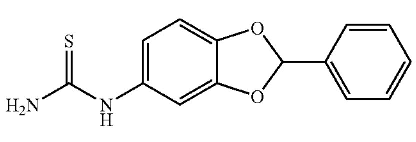 | 1-(2-phenylbenzo[d]-[1,3]dioxol-6-yl)thiourea |
| 20 | 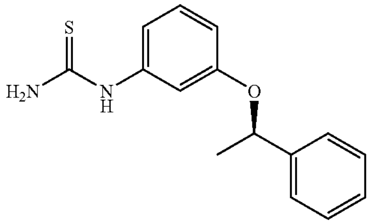 | 1-(3-((R)-1-phenylethoxy)phenyl)thiourea |

-continued

| CPD # | STRUCTURE | NAME |
|---|---|---|
| 21 | 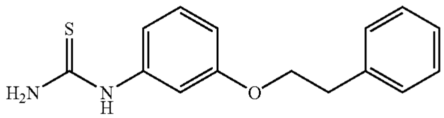 | 1-(3-(phenethyloxy)phenyl)thiourea |
| 22 | 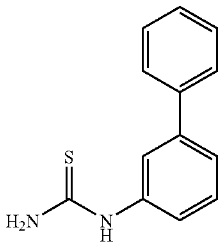 | 1-(3-(phenyl)phenyl)thiourea |
| 23 | 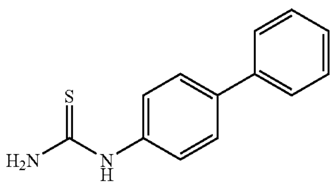 | 1-(4-(phenyl)phenyl)thiourea |
| 24 | 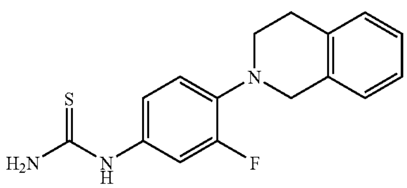 | 1-(3-fluoro-4-(3,4-dihydro-isoquinolin-2(1H)-yl)phenyl)thiourea |
| 25 | 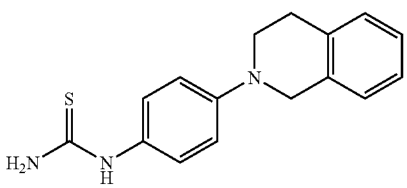 | 1-(4-(3,4-dihydro-isoquinolin-2(1H)-yl)phenyl)thiourea |
| 26 | 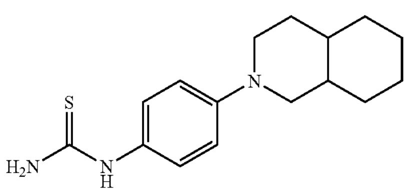 | 1-(4-(octahydroisoquinolin-2(1H)-yl)phenyl)thiourea |
| 27 | 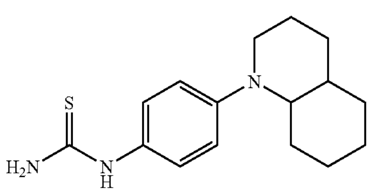 | 1-(4-(octahydroquinolin-1(2H)-yl)phenyl)thiourea |
| 28 | 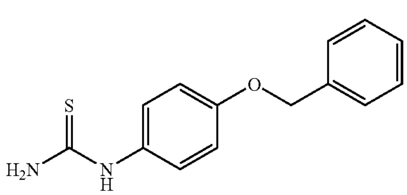 | 1-(4-(benzyloxy)phenyl)thiourea |

| CPD # | STRUCTURE | NAME |
|---|---|---|
| 29 | 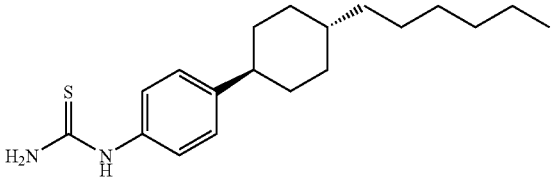 | 1-(4-((1s,4r)-4-hexylcyclohexyl)phenyl)thiourea |
| 30 | 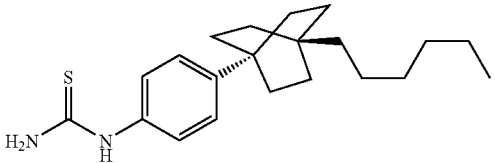 | 1-(4-(4-hexylbicyclo[2.2.2]octan-1-yl)phenyl)thiourea |
| 31 | 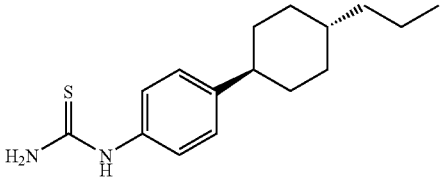 | 1-(4-((1s,4r)-4-propylcyclohexyl)phenyl)thiourea |
| 32 | 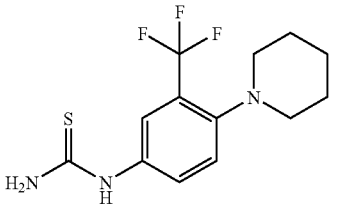 | 1-(3-(trifluoromethyl)-4-(piperidin-1-yl)phenyl)thiourea |
| 33 | 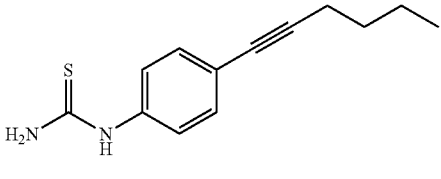 | 1-(4-(hex-1-ynyl)phenyl)thiourea |
| 34 | 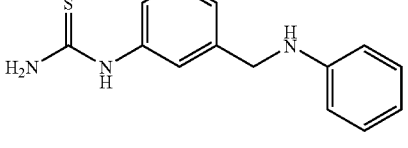 | 1-(4-(phenylamino-ethyl)phenyl)thiourea |
| 35 | 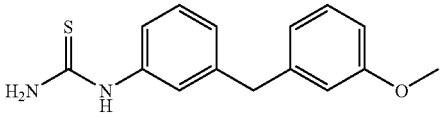 | 1-(3-(3-methoxybenzyl)phenyl)thiourea |
| 36 | 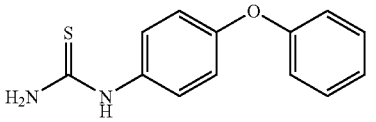 | 1-(4-phenoxyphenyl)thiourea |

| CPD # | STRUCTURE | NAME |
|---|---|---|
| 37 | 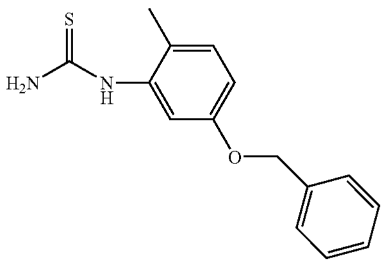 | 1-(5-(benzyloxy)-2-methylphenyl)thiourea |
| 38 | 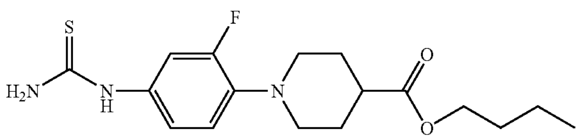 | butyl 1-(2-fluoro-4-thioureidophenyl)piperidine-4-carboxylate |
| 39 | 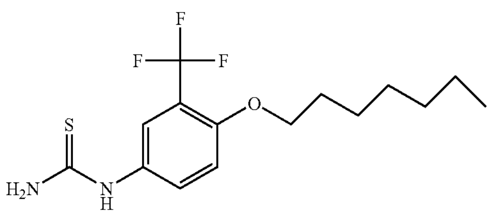 | 1-(4-(heptyloxy)-3-(trifluoromethyl)phenyl)thiourea |
| 40 | 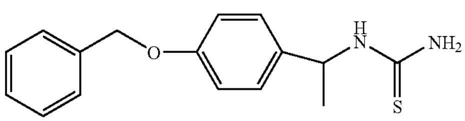 | 1-(1-(4-(benzyloxy)phenyl)ethyl)thiourea |
| 41 | 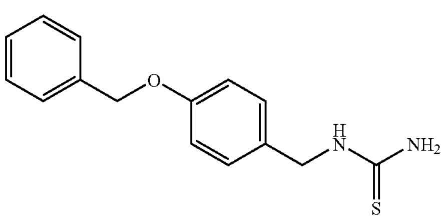 | 1-(4-(benzyloxy)benzyl)thiourea |
| 42 | 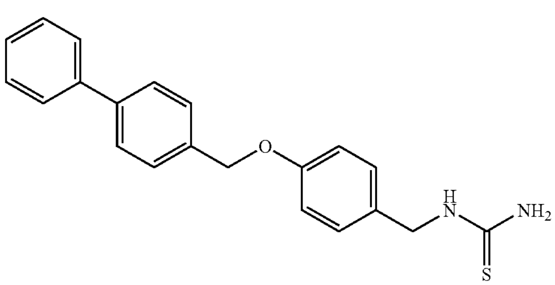 | 1-(4-(4-phenyl-benzyloxy)benzyl)thiourea |
| 43 | 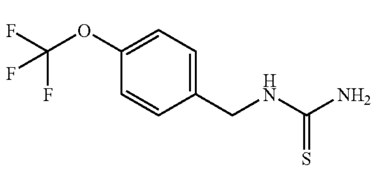 | 1-(4-(trifluoromethyl)benzyl)thiourea |

| CPD # | STRUCTURE | NAME |
|---|---|---|
| 44 | 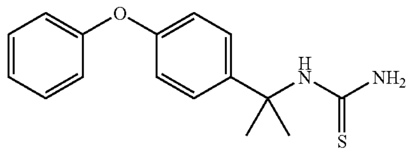 | 1-(2-(4-phenoxyphenyl)propan-2-yl)thiourea |
| 45 | 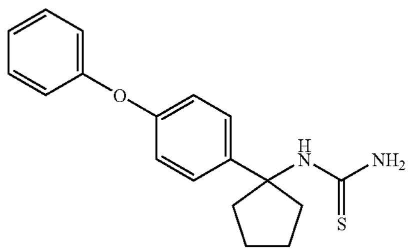 | 1-(1-(4-phenoxyphenyl)cyclopentyl)thiourea |
| 46 | 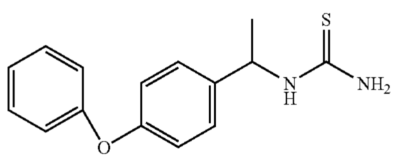 | 1-(1-(4-phenoxyphenyl)ethyl)thiourea |
| 47 | 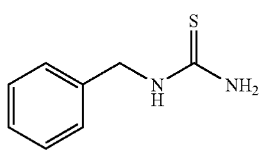 | 1-benzylthiourea |
| 48 | 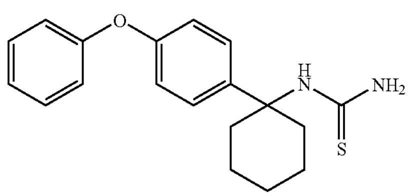 | 1-(1-(4-phenoxyphenyl)cyclohexyl)thiourea |
| 49 | 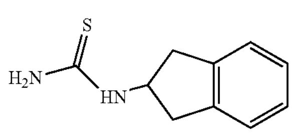 | 1-(2,3-dihydro-1H-inden-2-yl)thiourea |
| 50 | 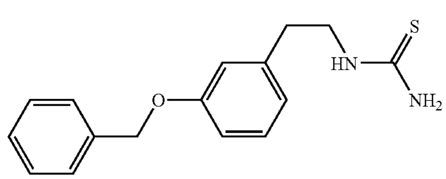 | 1-(3-(benzyloxy)phenethyl)thiourea |
| 51 | 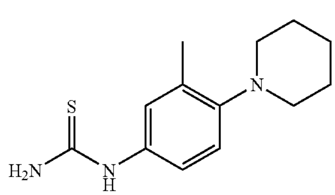 | 1-(3-(methyl)-4-(piperidin-1-yl)phenyl)thiourea |

| CPD # | STRUCTURE | NAME |
|---|---|---|
| 52 | 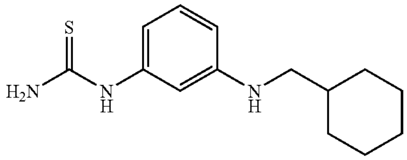 | 1-(3-(cyclohexylmethylamino)phenyl)thiourea |
| 53 | 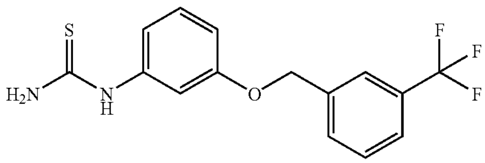 | 1-(3-(3-(trifluoromethyl)benzyloxy)phenyl)thiourea |
| 54 | 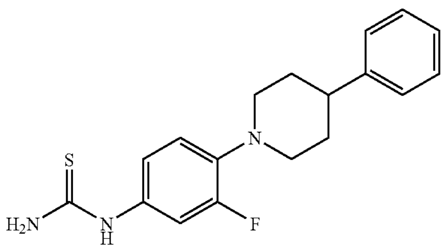 | 1-(3-fluoro-4-(4-phenylpiperidin-1-yl)phenyl)thiourea |
| 55 | 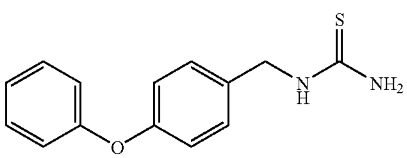 | 1-(4-phenoxybenzyl)thiourea |
| 56 | 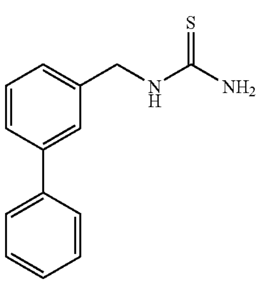 | 1-(3-phenylbenzyl)thiourea |
| 57 | 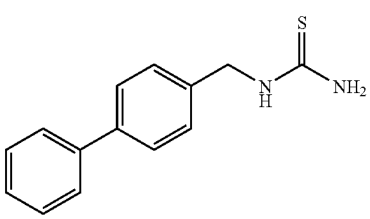 | 1-(4-phenylbenzyl)thiourea |
| 58 | 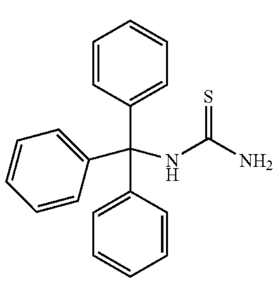 | 1-tritylthiourea |

-continued
| CPD # | STRUCTURE | NAME |
|---|---|---|
| 59 | 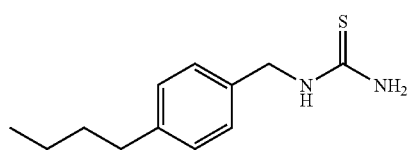 | 1-(4-butylbenzyl)thiourea |
| 60 | 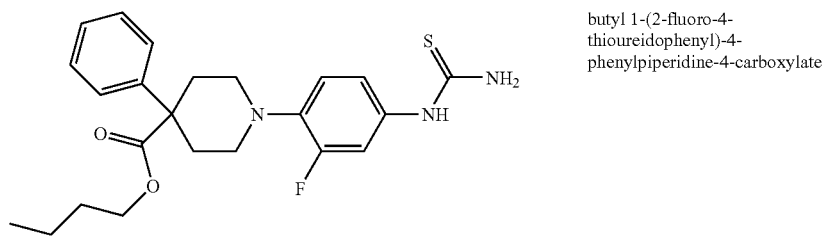 | butyl 1-(2-fluoro-4-thioureidophenyl)-4-phenylpiperidine-4-carboxylate |
| 61 | 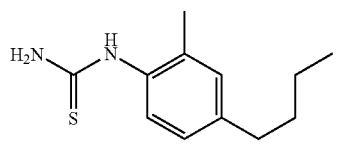 | 1-(4-butyl-2-methylphenyl)thiourea |
| 62 | 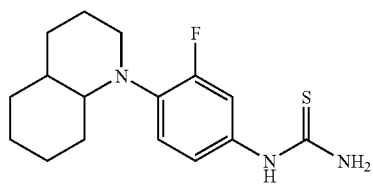 | 1-(3-fluoro-4-(octahydroquinolin-1(2H)-yl)phenyl)thiourea |
| 63 | 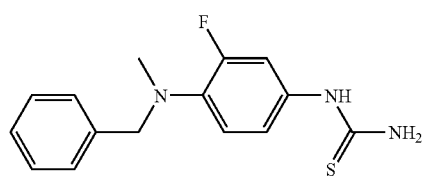 | 1-(4-(N-benzyl-N-methylamino)-3-fluorophenyl)thiourea |
| 64 | 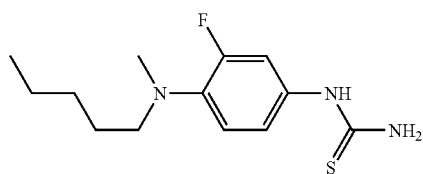 | 1-(4-(N-methyl-N-pentylamino)-3-fluorophenyl)thiourea |
| 65 | 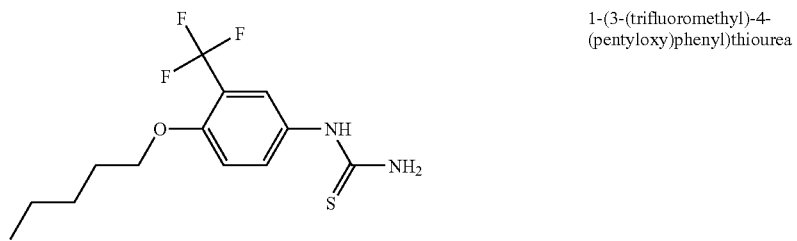 | 1-(3-(trifluoromethyl)-4-(pentyloxy)phenyl)thiourea |

Example 4

Synthesis OF N-(4-Phenoxyphenethyl)thiourea (Compound 66)

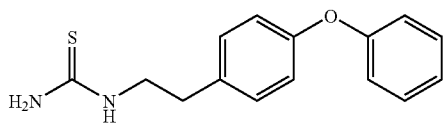

This compound is prepared via a method analogous to the method for preparation of N-(3-benzyloxyphenyl)thiourea using 4-phenoxyphenethylamine as the starting material. $^1$H NMR (CDCl$_3$, δ): 2.92 (t, J=6.9 Hz, 2H), 3.31-3.90 (m, 2H), 5.65 (s, 2H), 5.85-6.16 (m, 1H), 6.97-7.04 (m, 4H), 7.11-7.15 (m, 1H), 7.19 (d, J=7.4 Hz, 2H), 7.36 (t, J=7.8 Hz, 2H); LCMS (M+1): 273

Example 5

Synthesis of (3-Benzyl-phenyl)-thiourea (Compound 5)

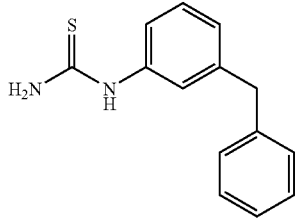

A solution of 3-benzylaniline (183 mg, 1 mmol) and 1,1'-thiocarbonyldiimidazole (197 mg, 1.1 mmol) in dichloromethane (5 ml) is stirred at room temperature for 1.5 hours. 2 M ammonia in methanol (2.5 ml) is added to the solution and the mixture is stirred at room temperature overnight. The solution is diluted with ethylacetate, and the organic layer is washed with 5% HCl, saturated NaHCO$_3$, and brine, and dried (anhydrous Na$_2$SO$_4$). The crude product is recrystallized from ethylacetate and petroleum ether to give the desired product as a white powder. $^1$H NMR (300 Hz, CDCl$_3$) δ 7.93 (br s, 1H, NH), 7.73-7.02 (m, 9H, Aryl H), 6.06 (br s, 2H, NH$_2$), 3.98 (s, 2H, CH$_2$). MS (APCI) m/z 243 [M+H]$^\pm$.

Example 6

Synthesis of (4-Pentyloxy-phenyl)-thiourea (Compound 6)

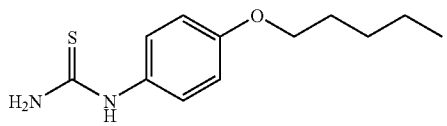

4-Pentyloxyaniline (370 ml, 2 mmol) in dichloromethane (3 ml) is added to a solution of 1,1'-thiocarbonyldiimidazole (537 mg, 3 mmol) in dichloromethane (5 ml) at room temperature and the mixture is stirred at room temperature for 30 minutes. 2 N Ammonia in methanol (30 ml) is added to the solution, and the solution is stirred for additional 1 hour at room temperature. The solvent is removed, and the product extracted with ethylacetate and H$_2$O. The crude product is recrystallized from dichloromethane and hexane to afford the thiourea as a white solid. $^1$H NMR (300 Hz, CDCl$_3$) δ 7.92 (s, 1H, NH), 7.15 (d, J=8.4 Hz, 2H, Aryl H), 6.92 (d, J=8.4 Hz, 2H, Aryl H), 6.0 (br s, 2H, NH$_2$), 3.95 (t, J=6.6 Hz, 2H, CH$_2$), 1.79 (m, 2H, CH$_2$), 1.44-1.38 (m, 4H, (CH$_2$)$_2$), 0.94 (t, J=7.2 Hz, 3H, CH$_3$). MS (APCI) m/z 239 [M+H]$^\pm$.

Example 7

Synthesis of 1-(4-(N-benzyl-N-methylamino)-3-fluorophenyl)thiourea (Compound 63)

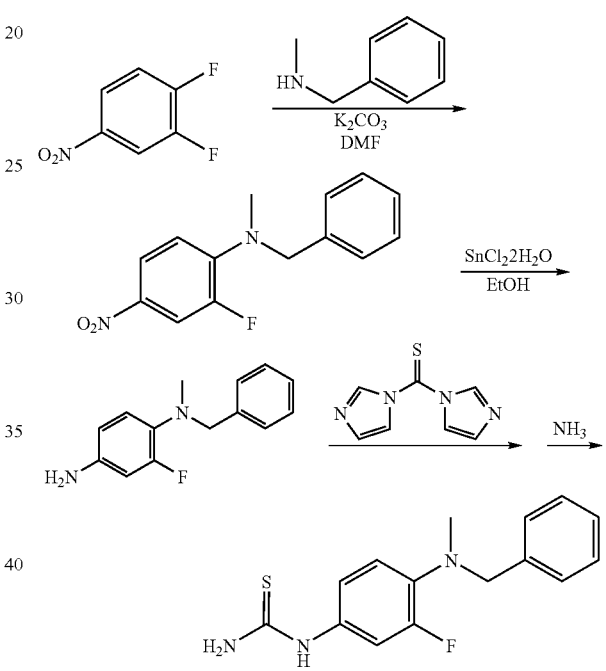

A solution of 1,2-difluoro-4-nitro-benzene (0.96 g, 6.0 mmole) and benzyl methylamine (0.79 g, 6.6 mmole) in 4 mL of anhydrous DMF is heated with K$_2$CO$_3$ (0.41 g, 3.0 mmole) at 80° C. for 16 hours. After removal of the solvent, the residue is purified on flash chromatography with EtOAc/Hexanes (0-15%), yielding yellow oil 1.05 g (4.0 mmole) 67% of benzyl-(2-fluoro-4-nitro-phenyl)-methylamine.

1.7 g (7.4 mmole) of Tin (II) chloride is added to a solution of benzyl-(2-fluoro-4-nitro-phenyl)-methylamine (0.60 g, 2.3 mmole) in 30 ml ethanol, and the reaction mixture is refluxed for 3 hours. After cooling, 2 N NaOH solution is added with stirring to adjust pH=8. The resulted mixture is filtered through a plug of Celite and the filtrate extracted with ethyl acetate. The organic layer is washed with brine and dried over Na$_2$SO$_4$, and concentrated to yield 0.52 g (2.2 mmole, 95%) of yellow oil N$^1$-Benzyl-2-fluoro-N$^1$-methyl-benzene-1,4-diamine MS: 231(M+1).

A solution of N$^1$-Benzyl-2-fluoro-N$^1$-methyl-benzene-1,4-diamine (23 mg, 0.1 mmole), and thiocarbonyl diimidazole (21 mg, 0.12 mmole) in 0.8 mL of dichloroethane is stirred at room temperature for 2 hours. Then 2M NH$_3$ in MeOH (0.4 mL, 0.4 mmloe) is added, and the reaction mixture is stirred at room temperature overnight. After removal of the solvent, the residue is purified on LC/MS to yield 6.3 mg pale colored oil product [4-(Benzyl-methyl-amino)-3-fluoro-phenyl]-thiourea. MS: 290(M+1).

Example 8

Synthesis of
(4-Pentyloxy-3-trifluoromethyl-phenyl)-thiourea
(Compound 65)

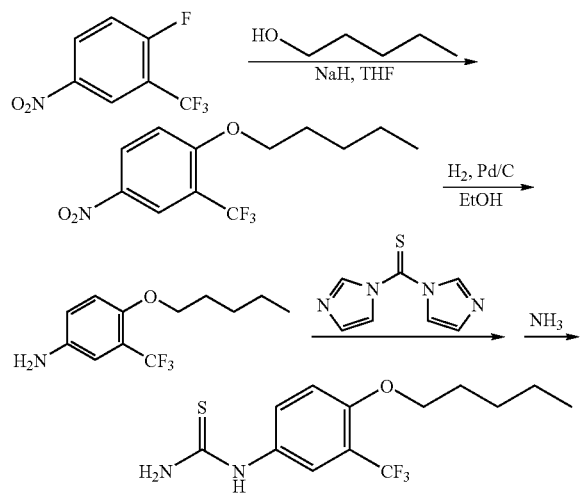

NaH (0.24 g, 6.0 mmole) is added to a solution of n-Pentanol (1.5 mL, excess) in 5 mL of THF at 0° C. After stirring at room temperature for 30 minutes, 1.0 g (5.0 mmole) of 1-Fluoro-4-nitro-2-trifluoromethyl-benzene is added, and the reaction mixture is stirred at room temperature overnight. After removal of the solvent, the residue is taken up in EtOAc. The organic layer is washed with 1N NaOH solution and brine, dried over $Na_2SO_4$, and concentrated to give the product as a yellow oil. The product is purified on flash chromatography with DCM/Hexanes (1/2) to yield pale yellow oil product 4-Nitro-1-pentyloxy-2-trifluoromethyl-benzene.

A solution of 4-Nitro-1-pentyloxy-2-trifluoromethyl-benzene (1.2 g, 4.8 mmole) and 0.1 g of 10% Palladium on activated carbon in 40 mL of ethanol is hydrogenated with hydrogen balloon at room temperature overnight. Filtration and concentration gave a pink oil 1.2 g (100%) of 4-Pentyloxy-3-trifluoromethyl-phenylamine MS: 248 (M+1).

A solution of 4-Pentyloxy-3-trifluoromethyl-phenylamine (25 mg, 0.1 mmole), and Thiocarbonyl diimidazole (21 mg, 0.12 mmole) in 1 mL of dichloromethane is stirred at room temperature for 2 hours. Then 2M $NH_3$ in MeOH (0.4 mL, 0.4 mmole) is added, and the reaction mixture is stirred at room temperature overnight. After removal of the solvent, the residue is washed with MeOH and water to yield pale solid product 4-Pentyloxy-3-trifluoromethyl-phenyl)-thiourea. MS: 307(M+1).

Example 9

Assay for Identifying Compounds which Inhibit HCV Replication

The compounds claimed herein were tested for the ability to inhibit viral replication of the Hepatitis C replicon in cultured cells in which the HCV replicon construct has been incorporated. The HCV replicon system was described by Bartenschlager, et. al (*Science,* 285, pp. 110-113 (1999)). The replicon system is predictive of in vivo anti-HCV activity; compounds that are active in humans uniformly evidence activity in the replicon assay.

HCV replicon-containing cells are treated with different concentrations of interferon alpha, a known inhibitor of HCV replication, as a positive control and with different concentrations of the test compound. The replicon assay system includes Neomycin Phosphotransferase (NPT) as a component of the replicon itself in order to detect the transcription of replicon gene products in the host cell. Cells in which the HCV is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

9A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

9B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin G418), screening media (DMEM supplemented with 10% FBS, L-glutamine, and non-essential amino acid, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu—N11, and enhancement solution.

HCV replicon-containing cells support high levels of viral RNA replicon replication when their density is suitable. Over confluency will cause a decrease of viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 ul/well (6-7.5×10$^5$ cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

9C. Treatment of HCV-Replicon Containing Cells with Test Compound

HCV replicon-containing cells are rinsed with once PBS once; 2 mls of trypsin is added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL 10131-035), 5 ml MEM non-essential amino acid (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 cells/100 μl/well of 96 well plate (6-7.5×10$^5$ cells/10 ml/plate). Plates are placed into 37° C. 5% $CO_2$ incubator overnight.

9D. Assay

The following morning, drugs (test compounds or interferon alpha) are diluted in 97 well U bottom plates with media or DMSO/media, depending on the final concentration chosen for the screening. Generally for 6 concentrations of each test compounds ranging from 10 micromolar to 0.03 micromolar are applied. 100 μl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NPTII assay is quantitated. The medium is poured from the plates and the plates are washed once in 200 μl of PBS. The PBS is then decanted and the plates tapped in a paper towel to remove any remaining PBS. Cells are fixed in situ with 100 μl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Cell viability may also be determined by CELLTITER 96 AQUEOUS ONE Solution Cell Proliferation Assay (Promega), a colorimetric assay for determining the number of viable cells. In this method, before fixing the cells, 10-20 μl MTS reagent is added to each well according to manufacturer's instruction, plates are incubated at 37° C. and read at OD 490 nm.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

Test Results:

Compounds 1, 3, 5-8, 12-42 and 44-59 were tested in this HCV replicon assay and found to be active inhibitors of HCV replicon replication; compounds 1, 3, 5-7, 12-16, 19-26, 28-35, 39, 51-57, and 59 display $EC_{50}$ values of less than 1 micromolar.

Example 10

Pharmaceutical Formulations

Examples 10A through 10G are examples of pharmaceutical compositions containing the compounds of Formula I. The abbreviation 'A.I.' stands for an arylthiourea viral inhibitor of the present invention.

Example 10A

Oral Drops 5 grams of A.I. is dissolved in 5 ml of 2-hydroxypropanoic acid and 15 ml polyethylene glycol at about 60°-80° C. After cooling to about 30°-40° C., 350 ml polyethylene glycol is added and the mixture was stirred well. A solution of 17.5 g sodium saccharin in 25 ml purified water is then added.

Flavor and polyethylene glycol q.s. (quantity sufficient) to a volume of 500 ml are added while stirring to provide an oral drop solution comprising 10 mg/ml of A.I.

Example 10B

Capsules 20 grams of the A.I., 6 grams sodium lauryl sulfate, 56 grams starch, 56 grams lactose, 0.8 grams colloidal silicon dioxide, and 1.2 grams magnesium stearate are vigorously stirred together. The resulting mixture is subsequently filled into 1000 suitable hardened gelatin capsules, comprising each 20 mg of the active ingredient.

Example 10C

Film-Coated Tablets

Preparation of tablet core: A mixture of 10 grams of the A.I., 57 grams lactose and 20 grams starch is mixed well and thereafter humidified with a solution of 0.5 grams sodium dodecyl sulfate, and 1.0 grams polyvinylpyrrolidone (KOLLIDON-K 90) in about 20 ml of water. The wet powder mixture is sieved, dried, and sieved again. Then 100 grams microcrystalline cellulose (AVICEL) and 15 grams hydrogenated vegetable oil (STEROTEX) are added. The whole is mixed well and compressed into tablets, giving 1000 tablets, each containing 10 mg of the active ingredient.

Coating: Ethyl cellulose (0.5 grams, ETHOCEL 22 CPS) in 15 ml of dichloromethane is added to a solution of 1.0 grams methyl cellulose (Methocel 60 HG®) in 7.5 ml of denatured ethanol. Then 7.5 ml of dichloromethane and 0.25 ml 1,2,3-propanetriol are added. Polyethylene glycol (1.0 grams) is melted and dissolved in 7.5 ml of dichloromethane and added to the cellulose-containing solution. Magnesium Octadecanoate (0.25 grams), 0.5 grams polyvinylpyrrolidone, and 3.0 ml of concentrated color suspension (OPASPRAY K-1-2109) are added and the whole mixture homogenized. The tablet cores are coated with this mixture in a coating apparatus.

Example 10D

Injectable Solutions 1.8 grams methyl 4-hydroxybenzoate and 0.2 grams propyl 4-hydroxybenzoate are dissolved in about 0.5 L of boiling water. After cooling to about 50° C., 4 grams lactic acid, 0.05 grams propylene glycol, and 4 grams of the A.M are added while stirring. The solution is cooled to room temperature and supplemented with water for injection q.s. giving a solution containing 4 mg/ml of A.I. The solution is sterilized by filtration and filled in sterile containers.

100.0 g of an acid salt of an A.I. of the invention is dissolved in boiling water. After cooling to about 50° C., 37.5 grams lactic acid (90% by weight) are added while stirring. The solution is cooled to room temperature and water is added to 1 L. The solution is sterilized by filtration and filled in sterile containers.

5.00 g of an acid salt of an A.I. of the invention is dissolved in boiling water. After cooling to about 50° C., 2.20 grams lactic acid (90% by weight) are added while stirring. The solution is cooled to room temperature and water is added to 100 ml.

Example 10E. Gel

A compound or salt of the invention may be formed as a gel for topical application.

A gel is prepared by suspending A.M (0.2 g-5.0 g) in benzyl alcohol at room temperature. A mixture of hydroxypropyl cellulose (2.5) grams and demineralized water (q.s. 100 g) is added to the suspension with stirring.

Example 10F

Cream

Phase I contains Sorbitan monostearate (2.0 g), Polyoxyethylene (20) sorbitan monostearate (1.5 g), Synthetic spermaceti (3.0 g) Cetyl stearyl alcohol (10.0 g) and 2-Octyldodecanol (13.5 g). The phase I mixture is heated to 75° C., stirred and mixed.

Phase II contains A.I. (1.0 g). Phase II is added to phase I, stirred and suspended.

Phase III contains Benzyl alcohol (1.0 g) and demineralized water (q.s. 100 g). Phase III is heated to 75° C. and added to phase II. The cream is mixed intensively and cooled slowly to room temperature, with further stirring. After cooling to room temperature the cream is homogenized.

Example 10G

Sprays

The active compound solutions or suspensions prepared according to Example 10D can also be processed to sprays. For this purpose, for example, a 60 to 90% active compound solution is mixed with 20 to 40% of the usual propellants, for example $N_2$, $N_2O$, $CO_2$, propane, butane, halogenohydrocarbons and the like.

The invention claimed is:
1. A compound having the formula

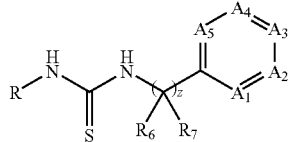

or a pharmaceutically acceptable salt thereof, wherein:
z is 0, 1, or 2;
R is hydrogen;
$R_1$, and $R_4$, and $R_5$ are each independently hydrogen, halogen, or methyl;
When z is 0;
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is
  (a) $C_3$-$C_6$alkyl or $C_3$-$C_6$alkoxy, each of which is substituted with at least one mono- or di-$C_1$-$C_4$alkylamino;
  (b) $C_4$-$C_8$alkoxycarbonyl;
  (c) (phenyl)$C_1$-$C_2$alkoxy, (phenyl)$C_1$-$C_2$alkylamino, (phenylamino)$C_1$-$C_2$alkyl, (cyclohexyl)$CH_2O$—, or indanyl-2-yloxy; or
  (d) (cyclohexyl)$C_0$-$C_2$alkyl or (piperidinyl)$C_0$-$C_2$alkyl, each of which is fused to a 6-membered carbocyclic ring;
wherein each of (a), (b), (c), and (d), is substituted with 0 to 3 substituents independently chosen from halogen, $C_1$-$C_4$alkyl, $C_1$-$C_4$alkoxy, mono- and di-($C_1$-$C_4$alkyl) amino, $C_1$-$C_2$haloalkyl, $C_1$-$C_2$haloalkoxy, and phenyl;
  (e) cyclohexyl, piperidinyl, or bridged cyclohexyl each of which is substituted with at least one substituent chosen from $C_2$-$C_6$alkoxycarbonyl, phenyl, $C_4$-$C_8$alkyl, and $C_4$-$C_8$alkoxy; and further substituted with 0 to 3 substituents independently chosen from halogen, $C_1$-$C_6$alkyl, $C_1$-$C_6$alkoxy, $C_1$-$C_2$haloalkyl, and $C_1$-$C_2$haloalkoxy;
  or one of $R_2$ and $R_3$ is halogen, $C_1$-$C_2$alkoxy, $C_1$-$C_2$haloalkyl, or $C_1$-$C_2$haloalkoxy, and the other is cyclohexyl, piperidinyl, $C_5$-$C_8$alkyl, $C_5$-$C_8$alkenyl, $C_5$-$C_8$alkynyl, or $C_4$-$C_8$alkoxy;
When z is 1 or 2,
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is
  (i) $C_3$-$C_6$alkyl or $C_3$-$C_6$alkoxy, substituted with at least one mono- or di-$C_1$-$C_4$alkylamino;
  (ii) $C_4$-$C_8$alkoxycarbonyl, $C_5$-$C_8$alkenyl, or $C_5$-$C_8$alkynyl;
  (iii) (phenyl)L which is optionally fused to a 6-membered carbocyclic ring or a 5- or 6-membered heterocyclic ring containing 1 or 2 heteroatoms independently chosen from N, O, and S;
    where L is $C_0$-$C_3$alkyl, —C(phenyl)$_2$-, $C_0$-$C_2$alkoxy, —O—$C_1$-$C_2$alkyl, or —NH—$C_1$-$C_2$alkyl-;
  (iv) (piperidinyl)$C_0$-$C_2$alkyl or (cyclohexyl)$C_0$-$C_2$alkyl or; each of which is optionally fused to a 6-membered carbocyclic ring;
  (v) bridged cyclohexyl;

wherein each of (i), (ii), (iii), (iv), and (v) is substituted with 0 to 3 substituents independently chosen from halogen, $C_1$-$C_4$alkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, and phenyl;

or one of $R_2$ and $R_3$ is halogen, $C_1$-$C_2$alkoxy, $C_1$-$C_2$haloalkyl, or $C_1$-$C_2$haloalkoxy, and the other is $C_5$-$C_8$alkyl or $C_4$-$C_8$alkoxy;

with the proviso that $R_2$ is not benzyloxy or cyclopentyloxy when $R_3$ is methoxy; and $R_6$ and $R_7$, when present, are independently chosen at each occurrence from hydrogen, methyl and ethyl; or $R_6$ and $R_7$ may be joined to form a 5- to 6-membered cycloalkyl ring.

2. A compound or salt of claim 1 in which $R_1$, $R_4$, and $R_5$ are all hydrogen.

3. A compound or salt of claim 1 wherein
z is 0;
one of $R_2$ and $R_3$ is hydrogen, $C_1$-$C_2$alkyl, or $C_1$-$C_2$alkoxy; and
the other of $R_2$ and $R_3$ is $C_4$-$C_8$alkoxycarbonyl.

4. A compound or salt of claim 1 in which
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is (phenyl)$C_1$-$C_2$alkoxy or (phenyl)$C_1$-$C_2$alkylamino, each of which is substituted with 0 to 3 substituents independently chosen from halogen, $C_1$-$C_4$alkyl, $C_1$-$C_4$alkoxy, $C_1$-$C_2$haloalkyl, $C_1$-$C_2$haloalkoxy, and phenyl.

5. A compound or salt of claim 1 wherein
z is 0;
one of $R_2$ and $R_3$ is hydrogen, $C_1$-$C_2$alkyl, or $C_1$-$C_2$alkoxy; and
the other of $R_2$ and $R_3$ is (e) (cyclohexyl)$C_0$-$C_2$alkyl or (piperidinyl)$C_0$-$C_2$alkyl, each of which is fused to a 6-membered carbocyclic ring; each of which (e) is substituted with 0 to 3 substituents independently chosen from halogen, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

6. A compound or salt of claim 1 wherein
z is 0;
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is cyclohexyl, piperidinyl, bridged cyclohexyl, each of which is substituted with at least one substituent chosen from $C_2$-$C_6$alkoxycarbonyl, phenyl, $C_4$-$C_8$alkyl, and $C_4$-$C_8$alkoxy; and further substituted with 0 to 3 substituents independently chosen from halogen, $C_1$-$C_6$alkyl, $C_1$-$C_6$alkoxy, $C_1$-$C_2$haloalkyl, and $C_1$-$C_2$haloalkoxy.

7. A compound of salt of claim 1 wherein
one of $R_2$ and $R_3$ is halogen, $C_1$-$C_2$alkyl, $C_1$-$C_2$alkoxy, $C_1$-$C_2$haloalkyl, or $C_1$-$C_2$haloalkoxy, and the other is cyclohexyl, piperidinyl, $C_5$-$C_8$alkyl, $C_5$-$C_8$alkenyl $C_5$-$C_8$alkynyl, or $C_4$-$C_8$alkoxy.

8. A compound or salt of claim 7 wherein one of $R_2$ and $R_3$ is chloro, fluoro, methoxy, trifluoromethyl, or trifluoromethoxy, and the other is cyclohexyl, piperidinyl, $C_5$-$C_8$alkyl, or $C_4$-$C_8$alkoxy.

9. A compound or salt of claim 1 wherein z is 1.

10. A compound or salt of claim 1 wherein z is 2.

11. A compound or salt of claim 9 wherein
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is $C_4$-$C_8$alkoxycarbonyl, $C_5$-$C_8$alkenyl, or $C_5$-$C_8$alkynyl.

12. A compound or salt of claim 9 wherein
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is (phenyl)L- which is substituted with 0 to 3 substituents independently chosen from chosen from halogen, $C_1$-$C_4$alkyl, $C_1$-$C_4$alkoxy, $C_1$-$C_2$haloalkyl, $C_1$-$C_2$haloalkoxy, and phenyl.

13. A compound or salt of claim 9 wherein
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is (piperidinyl)$C_0$-$C_2$alkyl or (cyclohexyl)$C_0$-$C_2$alkyl each of which is optionally bridged and each of which is substituted with 0 to 3 substituents independently chosen from chosen from halogen, $C_1$-$C_4$alkyl, $C_1$-$C_4$alkoxy, $C_1$-$C_2$haloalkyl, $C_1$-$C_2$haloalkoxy, and phenyl.

14. A compound or salt of claim 9 wherein
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is (piperidinyl)$C_0$-$C_2$alkyl or (cyclohexyl)$C_0$-$C_2$alkyl each of which is optionally fused to a phenyl, cyclohexyl, or cyclohexenyl ring;
each of which (piperidinyl)$C_0$-$C_2$alkyl or (cyclohexyl)$C_0$-$C_2$alkyl is substituted with 0 to 3 substituents independently chosen from chosen from halogen, $C_1$-$C_4$alkyl, $C_1$-$C_4$alkoxy, $C_1$-$C_2$haloalkyl, $C_1$-$C_2$haloalkoxy, and phenyl.

15. A compound or salt of claim 9 wherein
one of $R_2$ and $R_3$ is halogen, $C_1$-$C_2$alkoxy, $C_1$-$C_2$haloalkyl, or $C_1$-$C_2$haloalkoxy, and the other of $R_2$ and $R_3$ is $C_5$-$C_8$alkyl or $C_4$-$C_8$alkoxy.

16. A compound or salt of claim 1 wherein $R_6$ and $R_7$ are both hydrogen.

17. A compound or pharmaceutically acceptable salt thereof wherein the compound is:
1-(3-Benzyloxy)Phenylthiourea;
1-(4-Cyclohexylmethyloxy-phenyl)-thiourea;
1-(4-(3-(dimethylamino)propoxy)phenyl)thiourea;
1-[3-Fluoro-(4-(3-dimethylaminopropyloxy)phenyl)] thiourea;
1-(3-Fluoro-(4-Pentyloxy)-phenyl)-thiourea;
1-(3-(indan-2-yloxy)phenyl)thiourea;
1-(3-(3,4-difluorobenzyloxy)phenyl)thiourea;
1-(3-(4-phenylbenzyloxy)phenyl)thiourea;
1-(3-((S)-1-phenylethoxy)phenyl)thiourea;
butyl 4-phenyl-1-(3-thioureidophenyl)piperidine-4-carboxylate;
ethyl 4-phenyl-1-(3-thioureidophenyl)piperidine-4-carboxylate;
1-(3-((R)-1-phenylethoxy)phenyl)thiourea;
1-(3-(phenethyloxy)phenyl)thiourea;
1-(3-fluoro-4-(3,4-dihydro-isoquinolin-2(1H)-yl)phenyl) thiourea;
1-(4-(3,4-dihydro-isoquinolin-2(1H)-yl)phenyl)thiourea;
1-(4-(octahydroisoquinolin-2(1H)-yl)phenyl)thiourea;
1-(4-(octahydroquinolin-1(2H)-yl)phenyl)thiourea;
1-(4-(benzyloxy)phenyl)thiourea;
1-(4-((1s,4r)-4-hexylcyclohexyl)phenyl)thiourea;
1-(4-(4-hexylbicyclo[2.2.2]octan-1-yl)phenyl)thiourea;
1-(4-((1s,4r)-4-propylcyclohexyl)phenyl)thiourea;
1-(3-(trifluoromethyl)-4-(piperidin-1-yl)phenyl)thiourea;
1-(4-(phenylamino-ethyl)phenyl)thiourea;
1-(5-(benzyloxy)-2-methylphenyl)thiourea;
Butyl 1-(2-fluoro-4-thioureidophenyl)piperidine-4-carboxylate;
1-(4-(heptyloxy)-3-(trifluoromethyl)phenyl)thiourea;
1-(1-(4-(benzyloxy)phenyl)ethyl)thiourea;

1-(4-(benzyloxy)benzyl)thiourea;
1-(4-(4-phenyl-benzyloxy)benzyl)thiourea;
1-(2-(4-phenoxyphenyl)propan-2-yl)thiourea;
1-(1-(4-phenoxyphenyl)cyclopentyl)thiourea;
1-(1-(4-phenoxyphenyl)ethyl)thiourea;
1-(1-(4-phenoxyphenyl)cyclohexyl)thiourea;
1-(3-(benzyloxy)phenethyl)thiourea;
1-(3-(3-(trifluoromethyl)benzyloxy)phenyl)thiourea;
1-(3-fluoro-4-(4-phenylpiperidin-1-yl)phenyl)thiourea;
1-(4-phenoxybenzyl)thiourea;
butyl 1-(2-fluoro-4-thioureidophenyl)-4-phenylpiperidine-4-carboxylate;
1-(3-fluoro-4-(octahydroquinolin-1(2H)-yl)phenyl)thiourea;
1-(4-(N-benzyl-N-methylamino)-3-fluorophenyl)thiourea;
1-(4-(N-methyl-N-pentylamino)-3-fluorophenyl)thiourea;
1-(3-(trifluoromethyl)-4-(pentyloxy)phenyl)thiourea; or
N-(4-Phenoxyphenethyl)thiourea.

18. A pharmaceutical composition comprising a pharmaceutically acceptable carrier, diluent, or excipient, and a compound having the formula

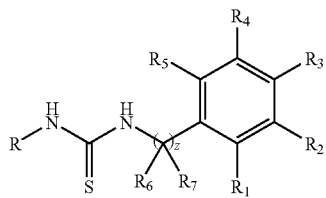

or a pharmaceutically acceptable salt thereof, wherein:
z is 0, 1, or 2;
R is hydrogen;
$R_1$, $R_4$, and $R_5$ are each independently hydrogen, halogen, or methyl;
When z is 0;
one of $R_2$ and $R_3$ is hydrogen $C_1$-$C_2$alkyl, $C_1$-$C_2$alkoxy, trifluoromethyl, or trifluoromethoxy; and
the other of $R_2$ and $R_3$ is
  (a) $C_3$-$C_6$alkyl or $C_3$-$C_6$alkoxy, each of which is substituted with at least one mono- or di-$C_1$-$C_4$alkylamino;
  (b) $C_4$-$C_8$alkoxycarbonyl;
  (c) (phenyl)ethyl, (phenyl)$C_1$-$C_2$alkoxy, indanyl-2-yloxy, (phenyl)$C_1$-$C_2$alkylamino, or (phenylamino)$C_1$-$C_2$alkyl,
  (d) (piperidinyl)$C_0$-$C_2$alkyl or (cyclohexyl)$C_0$-$C_2$alkyl or, each of which is optionally fused to a 6-membered carbocyclic ring; or
  (e) bridged cyclohexyl;
  wherein each of (a), (b), (c), (d), and (e), is substituted with 0 to 3 substituents independently chosen from halogen, $C_1$-$C_4$alkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, and phenyl;
or one of $R_2$ and $R_3$ is halogen, $C_1$-$C_2$alkoxy, $C_1$-$C_2$haloalkyl, or $C_1$-$C_2$haloalkoxy, and the other is cyclohexyl, piperidinyl, $C_5$-$C_8$alkyl, $C_5$-$C_8$alkenyl, $C_5$-$C_8$alkynyl, or $C_4$-$C_8$alkoxy;
When z is 1 or 2
one of $R_2$ and $R_3$ is hydrogen, hydroxy, amino, cyano, halogen, $C_1$-$C_6$alkyl, $C_1$-$C_6$alkoxy, $C_1$-$C_2$haloalkyl, or $C_1$-$C_2$haloalkoxy; and the other of $R_2$ and $R_3$ is
  (i) $C_3$-$C_6$alkyl or $C_3$-$C_6$alkoxy, substituted with at least one mono- or di-$C_1$-$C_4$alkylamino;
  (ii) $C_4$-$C_8$alkoxycarbonyl, $C_5$-$C_8$alkenyl, or $C_5$-$C_8$alkynyl;
  (iii) (phenyl)L- which is optionally fused to a 6-membered carbocyclic ring or a 5- or 6-membered heterocyclic ring containing 1 or 2 heteroatoms independently chosen from N, O, and S;
  (iv) (piperidinyl)$C_0$-$C_2$alkyl or (cyclohexyl)$C_0$-$C_2$alkyl each of which is optionally fused to a 6-membered carbocyclic ring; or
  (v) bridged cyclohexyl;
  wherein each of (i), (ii), (iii), (iv), and (v) is substituted with 0 to 3 substituents independently chosen from halogen, $C_1$-$C_4$alkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, and phenyl;
  or one of $R_2$ and $R_3$ is halogen, $C_1$-$C_2$alkoxy, $C_1$-$C_2$haloalkyl, or $C_1$-$C_2$haloalkoxy, and the other is $C_5$-$C_8$alkyl, or $C_4$-$C_8$alkoxy;
  with the proviso that $R_2$ is not benzyloxy or cyclopentyloxy when $R_3$ is methoxy; and
  $R_6$ and $R_7$, when present, are independently hydrogen, methyl and ethyl; or $R_6$ and $R_7$ may be joined to form a 5- to 6-membered cycloalkyl ring.

19. The pharmaceutical composition of claim 18, wherein the composition is formulated as an injectable fluid, an aerosol, a cream, a gel, a tablet, a pill, a capsule, a syrup, ophthalmic solution, or a transdermal patch.

20. A method of treating a Hepatitis C infection comprising administering to a human patient having a Hepatitis C infection a therapeutically effective amount of a compound having the formula

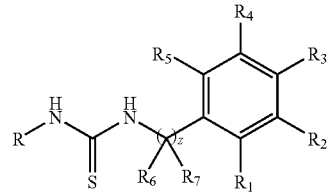

or a pharmaceutically acceptable salt thereof, wherein:
z is 0, 1, or 2;
R is hydrogen;
$R_1$, $R_4$, and $R_5$ are each independently hydrogen, halogen or methyl;
one of $R_2$ and $R_3$ is hydrogen, $C_1$-$C_2$alkyl, $C_1$-$C_2$alkoxy, trifluoromethyl, or trifluoromethoxy; and
the other of $R_2$ and $R_3$ is
  (i) $C_3$-$C_6$alkyl or $C_3$-$C_6$alkoxy, substituted with at least one mono- or di-$C_1$-$C_4$alkylamino;
  (ii) $C_4$-$C_8$alkoxycarbonyl, $C_5$-$C_8$alkyl, $C_5$-$C_8$alkenyl, $C_5$-$C_8$alkynyl; or $C_4$-$C_8$alkoxy;
  (iii) (phenyl)L- which is optionally fused to a 6-membered carbocyclic ring, where L is $C_0$-$C_3$alkyl, —C(phenyl)$_2$-, $C_0$-$C_2$alkoxy, —O—$C_1$-$C_2$alkyl, or —NH—$C_1$-$C_2$alkyl-; or
  (iv) (piperidinyl)$C_0$-$C_2$alkyl or (cyclohexyl)$C_0$-$C_2$alkyl, each of which is optionally fused to a 6-membered carbocyclic ring; or
  (v) bridged cyclohexyl;
  wherein each of (i), (ii), (iii), (iv), and (iv), is substituted with 0 to 3 substituents independently chosen from hydroxy, amino, cyano, halogen, $C_1$-$C_4$alkyl, $C_1$-$C_4$alkoxy, mono- and di-($C_1$-$C_4$alkyl)amino, $C_2$-$C_6$alkoxycarbonyl, $C_1$-$C_2$haloalkyl, $C_1$-$C_2$haloalkoxy, and phenyl; and $R_6$ and $R_7$, when present, are independently chosen from hydrogen, methyl and ethyl; or $R_6$ and $R_7$ may be joined to form a 5- to 6-membered cycloalkyl ring.

21. A compound having the formula

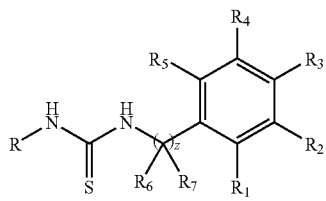

or a pharmaceutically acceptable salt thereof, wherein:

R is hydrogen;

z is 2;

$R_1$ and $R_4$ are each independently hydrogen, halogen, or methyl;

One of $R_2$ and $R_3$ is hydrogen, $C_1$-$C_2$alkyl, $C_1$-$C_2$alkoxy, trifluoromethyl, or trifluoromethoxy; and the other of $R_2$ and $R_3$ is (i) hydrogen, $C_1$-$C_2$alkyl, $C_1$-$C_2$alkoxy, trifluoromethyl, or trifluoromethoxy;

(ii) $C_3$-$C_6$alkyl or $C_3$-$C_6$alkoxy, substituted with at least one mono- or di-$C_1$-$C_4$alkylamino;

(iii) $C_4$-$C_8$alkoxycarbonyl, $C_5$-$C_8$alkyl, $C_5$-$C_8$alkenyl, $C_5$-$C_8$alkynyl; or $C_4$-$C_8$alkoxy;

(iv) (phenyl)L- which is optionally fused to a 6-membered carbocyclic ring, where L is $C_0$-$C_3$alkyl, —C(phenyl)$_2$-, $C_0$-$C_2$alkoxy, —O—$C_1$-$C_2$alkyl, or —NH—$C_1$-$C_2$alkyl-; or (v) (piperidinyl)$C_0$-$C_2$alkyl or (cyclohexyl)$C_0$-$C_2$alkyl, each of which is optionally fused to a 6-membered carbocyclic ring; or (vi) bridged cyclohexyl;

wherein each of (ii), (iii), (iv), (v), and (vi), is substituted with 0 to 3 substituents independently chosen from hydroxy, amino, cyano, halogen, $C_1$-$C_4$alkyl, $C_3$-$C_7$cycloalkyl, $C_1$-$C_4$alkoxy, mono- and di-($C_1$-$C_4$alkyl)amino, $C_1$-$C_2$haloalkyl, $C_1$-$C_2$haloalkoxy, phenyl, and pyridyl;

$R_5$ is joined with one of $R_6$ to form a fused 5- to 7-membered cycloalkyl ring; and the other of $R_6$ and both $R_7$ are independently chosen from hydrogen, methyl and ethyl; or $R_6$ and $R_7$ may be joined to form a 5- to 6-membered cycloalkyl ring.

22. A compound or pharmaceutically acceptable salt thereof, wherein the compound is 1-(3-(trifluoromethyl)-4-(pentyloxy)phenyl)thiourea.

* * * * *

UNITED STATES PATENT AND TRADEMARK OFFICE
CERTIFICATE OF CORRECTION

PATENT NO. : 7,718,671 B2  Page 1 of 1
APPLICATION NO. : 10/887227
DATED : May 18, 2010
INVENTOR(S) : Avinash Phadke et al.

It is certified that error appears in the above-identified patent and that said Letters Patent is hereby corrected as shown below:

Col. 54, Line 9-14, Delete formula shown, " 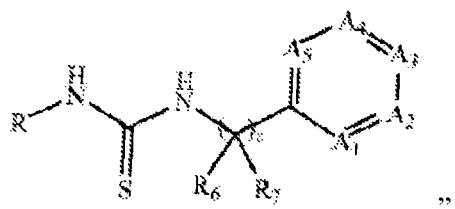 "

insert -- 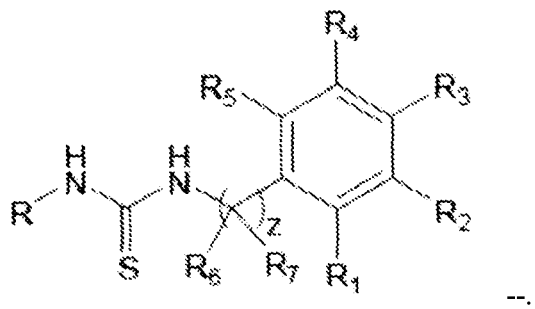 --.

Signed and Sealed this
Twenty-sixth Day of April, 2011

David J. Kappos
*Director of the United States Patent and Trademark Office*